US012035887B2

United States Patent
Nycz et al.

(10) Patent No.: US 12,035,887 B2
(45) Date of Patent: Jul. 16, 2024

(54) CLUTCH SYSTEM FOR FLEXIBLE ENDOSCOPES

(71) Applicants: BOSTON SCIENTIFIC SCIMED, INC., Maple Grove, MN (US); WORCESTER POLYTECHNIC INSTITUTE, Worcester, MA (US)

(72) Inventors: Christopher J. Nycz, Holden, MA (US); Elizabeth M. Albrecht, White Bear Lake, MN (US); Megan Chrobak, Groton, MA (US); Kianoosh Ghazi, Worcester, MA (US); Gregory Scott Fischer, Boston, MA (US); Bryan Allen Clark, Forest Lake, MN (US)

(73) Assignees: BOSTON SCIENTIFIC SCIMED, INC., Maple Grove, MN (US); WORCESTER POLYTECHNIC INSTITUTE, Worcester, MA (US)

( * ) Notice: Subject to any disclaimer, the term of this patent is extended or adjusted under 35 U.S.C. 154(b) by 144 days.

(21) Appl. No.: 17/532,240

(22) Filed: Nov. 22, 2021

(65) Prior Publication Data
US 2022/0160207 A1 May 26, 2022

Related U.S. Application Data

(60) Provisional application No. 63/117,626, filed on Nov. 24, 2020.

(51) Int. Cl.
*A61B 1/00* (2006.01)
*A61B 1/005* (2006.01)

(52) U.S. Cl.
CPC ........ *A61B 1/0052* (2013.01); *A61B 1/00039* (2013.01)

(58) Field of Classification Search
CPC .............. A61B 1/0052; A61B 1/00039; A61B 1/00006; A61M 25/0136
See application file for complete search history.

(56) References Cited

U.S. PATENT DOCUMENTS

| 4,461,282 A | 7/1984 | Ouchi et al. |
| 5,014,685 A * | 5/1991 | Takahashi ......... A61M 25/0136 600/148 |

(Continued)

FOREIGN PATENT DOCUMENTS

WO   2020049718 A1   3/2020

OTHER PUBLICATIONS

International Search Report and Written Opinion dated Feb. 28, 2022 for International Application No. PCT/US2021/060305.

(Continued)

*Primary Examiner* — Anh Tuan T Nguyen
*Assistant Examiner* — Rynae E Boler
(74) *Attorney, Agent, or Firm* — Seager, Tufte & Wickhem LLP

(57) ABSTRACT

An endoscopic system may include an endoscope including a handle and an elongate shaft extending distally therefrom. The handle may include a non-motorized and non-ratcheting actuation mechanism configured to articulate a distal tip portion of the elongate shaft. The distal tip portion may be articulatable in response to a manually applied force exerted upon the actuation mechanism. Removal of the manually applied force may lock the distal tip portion in its then-current configuration. The non-motorized and non-ratcheting actuation mechanism may include a clutch mechanism actuatable in response to an electrical signal generated in response to sensing a user-applied force to the actuating mechanism by a strain gauge.

16 Claims, 26 Drawing Sheets

(56) References Cited

U.S. PATENT DOCUMENTS

| | | | | |
|---|---|---|---|---|
| 5,578,052 | A | 11/1996 | Koros et al. | |
| 7,682,358 | B2 | 3/2010 | Gullickson et al. | |
| 7,686,816 | B2 | 3/2010 | Belef et al. | |
| 8,808,168 | B2* | 8/2014 | Ettwein | A61B 1/0052 600/149 |
| 9,375,550 | B2 | 6/2016 | Tegg | |
| 9,402,604 | B2 | 8/2016 | Williams et al. | |
| 2004/0267093 | A1* | 12/2004 | Miyagi | A61B 1/009 600/152 |
| 2010/0191224 | A1* | 7/2010 | Butcher | A61B 34/76 606/1 |
| 2010/0210908 | A1* | 8/2010 | Ashida | A61B 1/0016 600/145 |
| 2015/0335862 | A1* | 11/2015 | Selkee | A61B 5/287 604/95.04 |
| 2016/0270825 | A1* | 9/2016 | Wentz | A61B 17/7016 |
| 2017/0325659 | A1* | 11/2017 | Wang | A61B 1/0052 |
| 2017/0325660 | A1* | 11/2017 | Wang | A61B 1/0052 |
| 2019/0313881 | A1 | 10/2019 | Francher | |
| 2021/0393115 | A1* | 12/2021 | Sciortino | A61B 1/00042 |

OTHER PUBLICATIONS

Asge, "Minimizing Occupational Hazards in Endoscopy: Personal Protective Equipment, Radiation Safety, and Ergonomics," Gastrointestinal Endoscopy Journal, vol. 72, No. 2, 9 pp. 227-235, 2010.

Cho et al; "Evaluation of Performance Parameters of the Disposable Flexible Ureterorenoscope (LITHOVUE) in Patients with Renal Stones: A Prospective, Observational, Single-Arm, Multicenter Study," Scientific Reports, vol. 8:9795, 6 pages, Published online: Jun. 28, 2018.

Tian et al; "Cannulation Time is a More Accurate Measure of Cannulation Difficulty in Endoscopic Retrograde Cholangiopancreatography than the Number of Attempts," Gastroenterology Report, 1, pp. 193-197, Aug. 2013.

Tringali et al; "Endoscopic Retrograde Cholangiopancreatography: Indications, Patient Preparation and Complications," UpToDate®, Wolters Kluwer® 33 pages, Accessed Sep. 1, 2020.

* cited by examiner

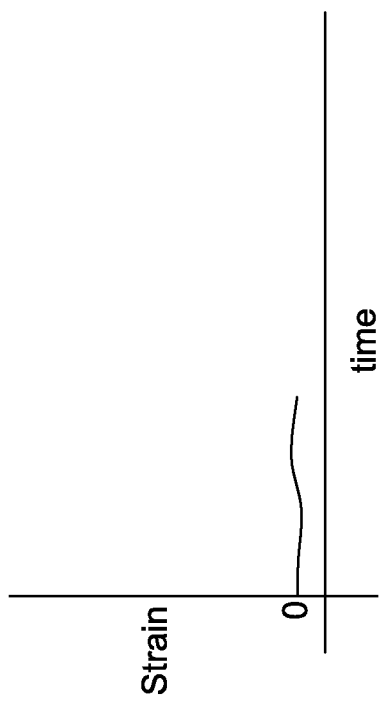
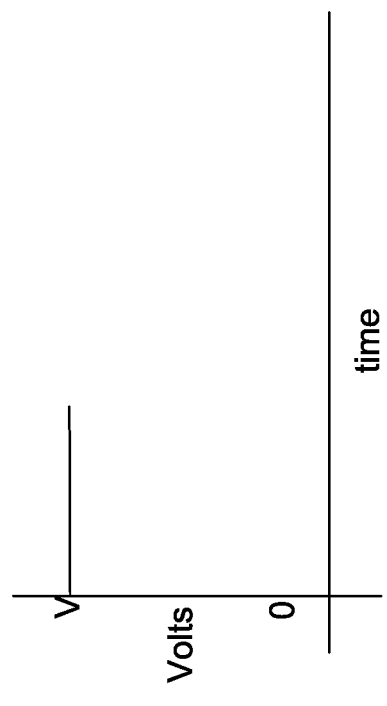

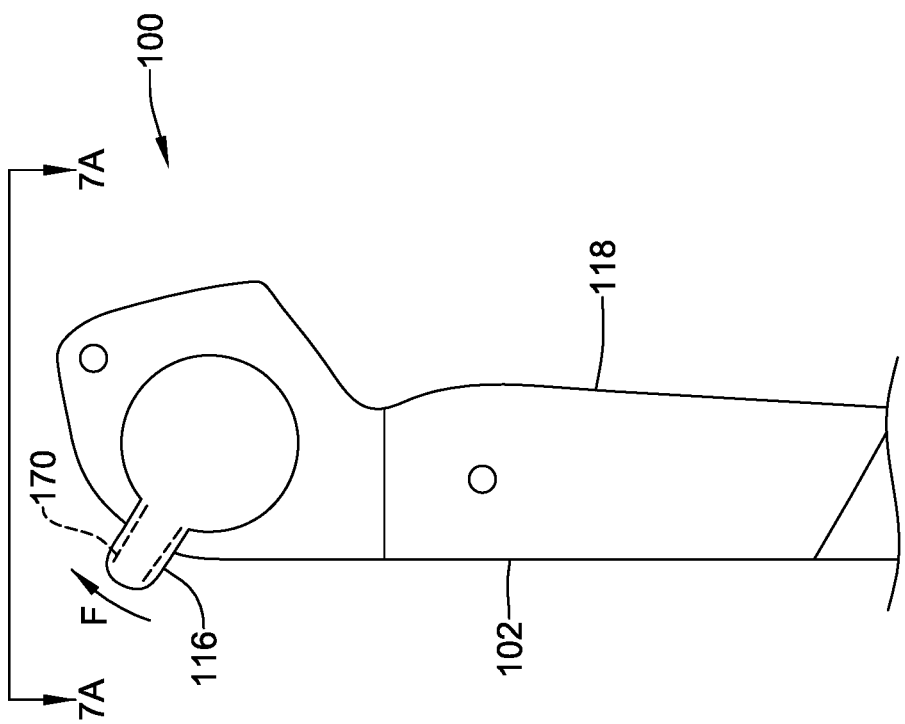

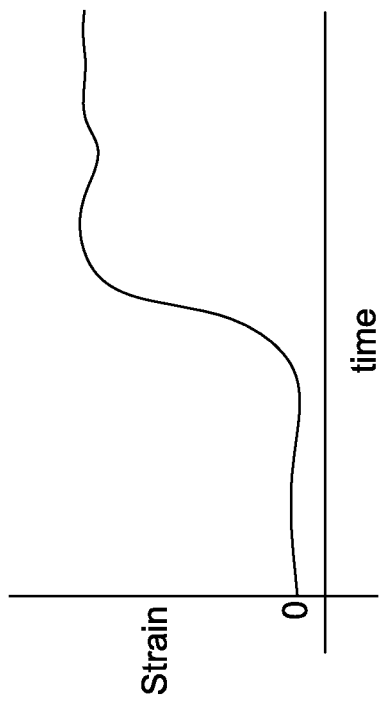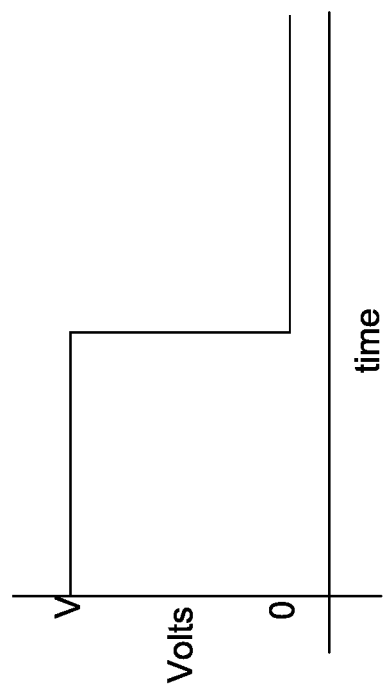

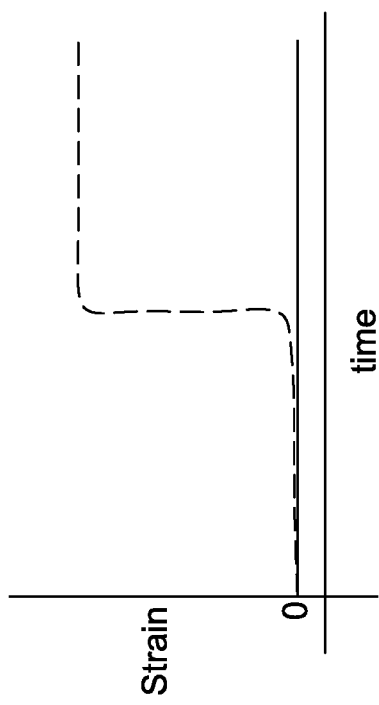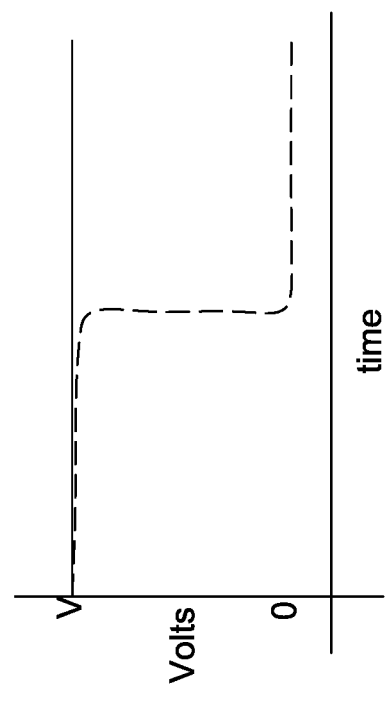

CLUTCH SYSTEM FOR FLEXIBLE ENDOSCOPES

CROSS REFERENCE TO RELATED APPLICATIONS

The present application claims the benefit of and priority to US Provisional Patent Application No. 63/117,626, filed Nov. 24, 2020, the disclosure of which is incorporated herein by reference.

TECHNICAL FIELD

The disclosure is directed to an endoscopic system. More particularly, the disclosure is directed to an endoscopic system having a clutch mechanism configured to control movement of an articulating distal tip.

BACKGROUND

An endoscopic system may be used to perform various diagnostic and/or treatment procedures. Different procedures may require different devices and/or different physical actions by the practitioner. Of the known medical devices, systems, and methods, each has certain advantages and disadvantages. There is an ongoing need to provide alternative medical devices and systems.

SUMMARY

In one example, an endoscopic system may comprise an endoscope including a handle and an elongate shaft extending distally therefrom. The handle may include a non-motorized and non-ratcheting mechanism configured to articulate a distal tip portion of the elongate shaft. The distal tip portion may be articulatable in response to a manually applied force exerted upon the handle. Removal of the manually applied force may lock the distal tip portion in its then-current configuration.

In addition or alternatively to any example disclosed herein, the non-motorized and non-ratcheting mechanism includes an actuator disposed on an exterior of the handle.

In addition or alternatively to any example disclosed herein, the actuator includes a rotatable knob configured to articulate the distal tip portion.

In addition or alternatively to any example disclosed herein, the actuator includes a lever configured to articulate the distal tip portion.

In addition or alternatively to any example disclosed herein, the non-motorized and non-ratcheting mechanism includes a clutch mechanism actuatable in response to an electrical signal, the clutch mechanism being configured to prevent articulation of the distal tip portion when the electrical signal is changed (e.g., received).

In addition or alternatively to any example disclosed herein, the non-motorized and non-ratcheting mechanism includes a strain gauge configured to detect the manually applied force.

In addition or alternatively to any example disclosed herein, the electrical signal is changed (e.g., interrupted) in response to a strain detected using the strain gauge.

In addition or alternatively to any example disclosed herein, the clutch mechanism is released when the manually applied force is detected using the strain gauge.

In addition or alternatively to any example disclosed herein, the non-motorized and non-ratcheting mechanism includes a touch sensor configured to detect a user's hand in contact with the non-motorized and non-ratcheting mechanism.

In addition or alternatively to any example disclosed herein, the endoscope includes an actuatable button disposed on the handle, the actuatable button being configured to interrupt the electrical signal to the clutch mechanism when the actuatable button is depressed.

In addition or alternatively to any example disclosed herein, the electrical signal is sent to the clutch mechanism when the actuatable button is released.

In addition or alternatively to any example disclosed herein, in another example, an endoscopic system may include an endoscope including a handle and an elongate shaft extending distally therefrom. The endoscopic system may also include an actuation mechanism configured to articulate a distal tip portion of the elongate shaft. The endoscopic system may also include a clutch mechanism actuatable between an engaged configuration and a disengaged configuration. The distal tip portion is articulatable in response to a manually applied force exerted upon the actuation mechanism. In response to a first electrical signal level generated when no manual force is exerted upon the actuation mechanism, the clutch mechanism is in the engaged configuration to prevent articulation of the distal tip portion, and in response to a second electrical signal level generated when a manually applied force above a threshold amount is exerted upon the actuation mechanism, the clutch mechanism is in the disengaged configuration to permit articulation of the distal tip portion. Removal of the manually applied force shifts the clutch mechanism to the engaged configuration and locks the distal tip portion in its then-current configuration.

In addition or alternatively to any example disclosed herein, and in another example, an endoscopic system may comprise an endoscope including a handle and an elongate shaft extending distally therefrom, wherein the handle may include a first non-motorized and non-ratcheting mechanism configured to articulate a distal tip portion of the elongate shaft in a first plane, and a second non-motorized and non-ratcheting mechanism configured to articulate the distal tip portion of the elongate shaft in a second plane different from the first plane. The distal tip portion may be articulatable in response to a manually applied force exerted upon the handle. Removal of the manually applied force may lock the distal tip portion in its then-current configuration.

In addition or alternatively to any example disclosed herein, the first non-motorized and non-ratcheting mechanism includes a first clutch mechanism actuatable in response to a first electrical signal, the first clutch mechanism being configured to prevent articulation of the distal tip portion in the first plane when the first electrical signal is received.

In addition or alternatively to any example disclosed herein, the second non-motorized and non-ratcheting mechanism includes a second clutch mechanism actuatable in response to a second electrical signal, the second clutch mechanism being configured to prevent articulation of the distal tip portion in the second plane when the second electrical signal is received.

In addition or alternatively to any example disclosed herein, and in another example, an accessory clutch system for use with articulating endoscopes may comprise a housing configured to matingly attach to a handle of an endoscope, wherein the handle includes a non-motorized and non-ratcheting mechanism configured to articulate a distal tip portion; and a clutch mechanism secured to the housing.

The clutch mechanism may be configured to releasably engage an actuator of the endoscope. The actuator may be disposed on an exterior of the handle. The housing may include a retaining structure configured to engage (e.g., encircle) at least a portion of the handle. The distal tip portion may be articulatable in response to a manually applied force exerted upon the handle. Removal of the manually applied force may lock the distal tip portion in its then-current configuration.

In addition or alternatively to any example disclosed herein, the clutch mechanism is actuatable in response to an electrical signal, the clutch mechanism being configured to prevent articulation of the distal tip portion when the electrical signal is at a first signal level.

In addition or alternatively to any example disclosed herein, a strain gauge is configured to detect the manually applied force.

In addition or alternatively to any example disclosed herein, the electrical signal is changed from the first signal level to a second signal level in response to a strain detected using the strain gauge.

In addition or alternatively to any example disclosed herein, the housing includes an actuatable button disposed thereon, the actuatable button being configured to change the electrical signal to the clutch mechanism from the first signal level to a second signal level when the actuatable button is depressed.

In addition or alternatively to any example disclosed herein, the first signal level is sent to the clutch mechanism when the actuatable button is released.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

Embodiments of the disclosure may be more completely understood in consideration of the following detailed description in connection with the accompanying drawings, in which:

FIGS. 6A-6B are graphs illustrating interactions between different characteristics of the clutch mechanism of FIGS. 5-5A;

FIG. 7 illustrates selected aspects of the clutch mechanism in the endoscopic system of FIG. 5;

FIGS. 8A-8B are graphs illustrating interactions between different characteristics of the clutch mechanism of FIGS. 7-7A;

FIGS. 14A-14B are graphs illustrating interactions between different characteristics of the clutch mechanism of FIGS. 13-13A;

Figure 1A:
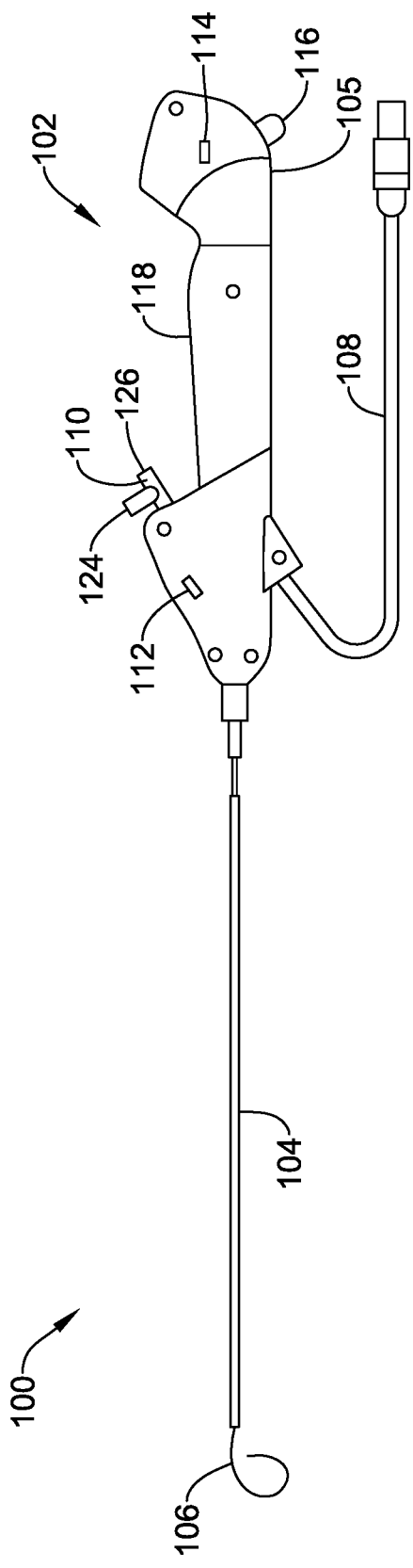
FIGS. 1A-1B are schematic illustrations of selected aspects of an endoscopic system.

While the embodiments of the present disclosure are amenable to various modifications and alternative forms, specifics thereof have been shown by way of example in the drawings and will be described in detail. It should be understood, however, that the intention is not to limit aspects of the present disclosure to the particular embodiments described. On the contrary, the intention is to cover all modifications, equivalents, and alternatives falling within the spirit and scope of the present disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claims. Those skilled in the art will recognize that the various elements described and/or shown may be arranged in various combinations and configurations without departing from the scope of the disclosure. The detailed description and drawings illustrate example embodiments. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the embodiments of the present disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Some endoscopic procedures—for example: kidney stone management, ERCP (endoscopic retrograde cholangiopancreatography), pulmonary biopsy, colonoscopy, bladder mapping, cardiac mapping, cardiac valve replacement and/or repair, and others—may require navigation through tortuous anatomy to position the medical device(s) at a specific location and/or orientation. Some of these procedures may be long and/or may involve difficult physical actions that may lead to physician fatigue. In some endoscopic procedures, the physician may be at risk of work-related strain due to repetitive motions, prolonged awkward posture(s), high forces, contact stress, and/or vibration. For example, some physicians may be at risk to develop De Quervain's tenosynovitis (swelling and pain at the base of the thumb), carpal tunnel syndrome, ganglion cysts, "trigger finger", and/or other conditions. Maintaining the stability of the endoscope and/or the position of the endoscope during procedures may lead to physician fatigue, may cause physicians to lose optimal positioning for the intended procedure, may lengthen procedures, and/or may cause complications, particularly with endoscopes having a distal tip that is steerable and/or articulatable. Such devices may be configured to and/or may be prone to returning to an "at-rest" position when steering and/or articulation forces are removed and/or not held constant by the physician. Manual locking features and/or switches require additional hand manipulation by the physician, thus exacerbating the physician's fatigue. The current disclosure relates to features that reduce and/or eliminate manual hand manipulation required by the physician to maintain the stability and/or orientation of the endoscope while reducing physician fatigue resulting from the procedures.

Figure 1B:
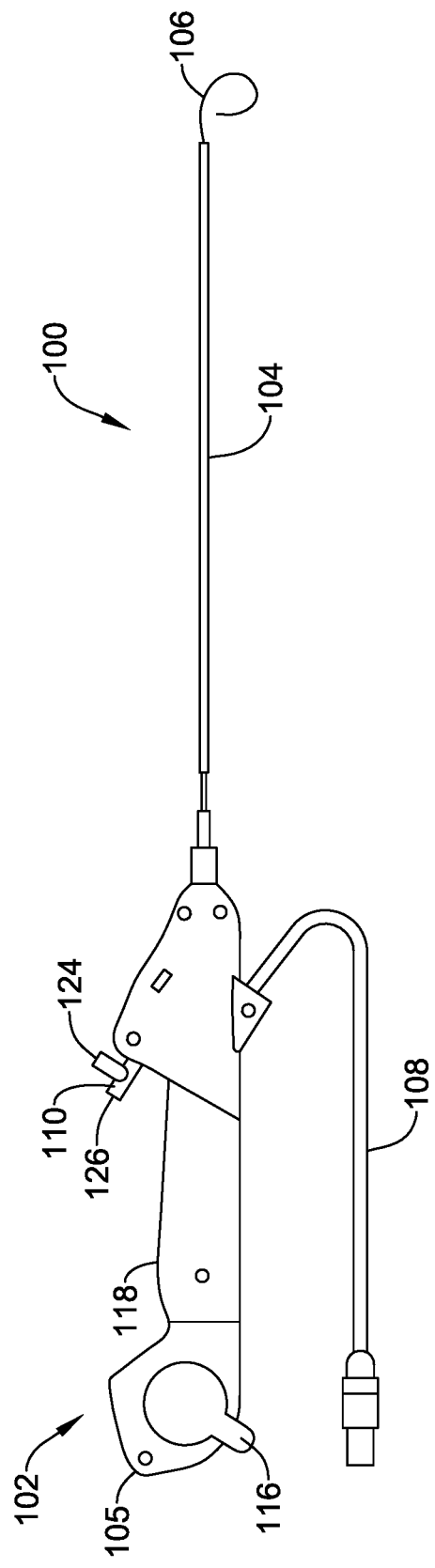

FIGS. 1A-1B illustrate aspects of an endoscopic system that may be used in conjunction with other aspects of the disclosure. In some embodiments, the endoscopic system may include an endoscope 100. The endoscope 100 may be specific to a particular endoscopic procedure, such as, e.g., ureteroscopy, or may be a general-purpose device suitable for a wide variety of procedures. In some embodiments, the endoscope 100 includes a handle 102 and an elongate shaft 104 extending distally therefrom, wherein the handle 102 includes a non-motorized and non-ratcheting mechanism configured to articulate a distal tip portion 106 of the elongate shaft 104 at and/or proximate a distal end thereof. The distal tip portion 106 may include a camera and may, for example, have deflection and/or articulation capabilities in one or more directions for viewing patient anatomy. In some embodiments, the endoscope 100 may be a ureteroscope such as a LithoVue™ scope. However, other medical devices, such as another endoscope or related system, (e.g., SpyScope™ DS, SpyGlass™ DS, Exalt™ Model D, etc.) may be used in addition to or in place of a ureteroscope. In some embodiments, the endoscope 100 may be configured to deliver fluid from a fluid management system to a treatment site via the elongate shaft 104. The elongate shaft 104 may include one or more working lumens for receiving a flow of fluid and/or other medical devices therethrough. In some embodiments, the endoscope 100 may be connected to the fluid management system via one or more supply line(s).

In some embodiments, the handle 102 of the endoscope 100 may include a plurality of elements configured to facilitate the endoscopic procedure. In some embodiments, a cable 108 extends from the handle 102 and is configured for attachment to an electronic device (not pictured) such as e.g. a computer system, a console, a microcontroller, etc. for providing power, analyzing endoscopic data, controlling the endoscopic intervention, or performing other functions. In some embodiments, the electronic device to which the cable 108 is connected may have functionality for recognizing and exchanging data with other endoscopic accessories. The handle 102 may include a grip area 118 for the operating physician to grasp while performing the endoscopic procedure. The handle 102 and/or the non-motorized and non-ratcheting mechanism may include an actuator 116 disposed on an exterior of the handle 102 at a proximal end 105 of the handle 102, wherein the actuator 116 may be actuated to control articulation of the distal tip portion 106. In some embodiments, the actuator 116 may be movably coupled to the handle 102. In some embodiments, the actuator 116 may be configured to engage with and/or actuate the non-motorized and non-ratcheting mechanism.

In some embodiments, the distal tip portion 106 may be articulatable in response to a manually applied force exerted upon the handle 102 and/or elements thereof (e.g., the actuator 116, etc.) as described herein. In one example, the actuator 116 may include a lever configured to articulate the distal tip portion 106 of the endoscope 100. In another example, the actuator 116 may include a rotatable knob configured to articulate the distal tip portion 106 of the endoscope 100. As will be discussed in more detail herein, removal of the manually applied force may lock the distal tip portion 106 in its then-current configuration and/or position.

In some embodiments, the endoscope 100 may include a pulley or rotating member (e.g., FIG. 3) disposed within the handle 102 and operatively connected to the distal tip portion 106. In some embodiments, one or more cables, wires, or other filaments may be engaged with and/or connected to the pulley within the handle 102. In some embodiments, the one or more cables, wires, or filaments may be engaged with and/or connected to the distal tip portion 106, such that tension applied to the one or more cables, wires, or filaments by the pulley moves and/or articulates the distal tip portion 106.

In some embodiments, the endoscope 100 may be in electronic communication with a workstation via a wired connection (e.g., the cable 108). In some embodiments, the workstation may include a touch panel computer, an interface box for receiving the wired connection (e.g., the cable 108), a cart, and a power supply, among other features. In some embodiments, the interface box may be configured with a wired or wireless communication connection with the controller of the fluid management system. The touch panel computer may include at least a display screen and an image processor, and in some embodiments, may include and/or define a user interface. In some embodiments, the workstation may be a multi-use component (e.g., used for more than one procedure) while the endoscope 100 may be a single use device, although this is not required. In some embodiments, the workstation may be omitted and the endoscope 100 may be electronically coupled directly to the controller of the fluid management system.

In some embodiments, the handle 102 may include at least one communication interface for attaching accessory devices. In some embodiments, the handle 102 has a first communication interface 112 and second communication interface 114. In one example, the first communication interface 112 and/or the second communication interface 114 may include Universal Serial Bus type-C (USB-C) ports, Universal Serial Bus (USB) ports, ethernet ports, and/or other types of ports. In some embodiments, more, less, and/or other communication interfaces of various types, including, for example, custom interfaces, may be used. In some embodiments, the handle 102 has only one communication interface but may be connectable to e.g. a USB hub with multiple ports for connecting multiple accessories. In some embodiments, the first communication interface 112 and/or the second communication interface 114 may provide power to the accessory device(s) in addition to exchanging data therewith. Thus, the accessory device(s) need not have separate cables running to a connected electronic device or a battery that adds additional weight to the handle 102. In some embodiments, the accessory device(s) may be uniquely associated with the endoscope 100 and recognized by the electronic device through "plug and play" functionality without any user setup required.

In some embodiments, a T-connector 110 extends from a distal portion of the handle 102 and provides a first port 124 and a second port 126 for accessing the working channel of the elongate shaft 104. In some embodiments, the first port 124 and the second port 126 are arranged perpendicularly to one another with the first port 124 facing distally and the second port 126 facing proximally. An accessory device or an elongated end effector device may be passed through either one of the first port 124 and the second port 126, however, the second port 126 may be preferred when the device is proximal to the T-connector 110. In another embodiment, a Y-connector may be used with first and second ports both facing proximally, such that two devices may be passed into the working channel of the elongate shaft 104 from a position proximal to the Y-connector. Other configurations are also contemplated.

In some embodiments, the endoscope 100 may include one or more sensors proximate the distal tip portion 106 and/or the distal end of the elongate shaft 104. For example, the endoscope 100 may include a pressure sensor at the distal tip portion 106 of the elongate shaft 104 to measure intracavity pressure within the treatment site. The endoscope 100 may also include other sensors such as, for example, a temperature sensor, a Fiber Bragg grating optical fiber to detect stresses, and/or an antenna or electromagnetic sensor (e.g., a position sensor). In some embodiments, the distal tip portion 106 and/or the distal end of the endoscope 100 may also include at least one camera to provide a visual feed to the user on the display screen of the touch panel computer. In another embodiment, the endoscope 100 may include two cameras having different communications requirements or protocols so that different information may be relayed to the user by each camera. When so provided, the user may switch back and forth between the cameras at will through the touch screen interface and/or the touch panel computer. While not explicitly shown, the elongate shaft 104 may include one or more working lumens for receiving the fluid and/or other medical devices.

In some embodiments, the location of the distal tip portion 106 and/or the distal end of the elongate shaft 104 may be tracked during use. For example, a mapping and navigation system may include an operating table (or other procedural or examination table or chair, etc.) configured to act or function as an electromagnetic generator to generate a magnetic field of a known geometry. Alternatively, or additionally, an electromagnetic generator separate from the operating table may be provided. The operating table and/or the electromagnetic generator may be coupled to a control unit which may include among other features, a processor, a memory, a display, and an input means. A position sensor (e.g., the electromagnetic sensor, etc.) or antenna, may be incorporated into the distal tip portion 106 and/or the distal end of the elongate shaft 104 of the endoscope 100. The position sensor may be configured for use in sensing a location of the position sensor in the magnetic field of the mapping and navigation system. In some embodiments, the position sensor may be electronically coupled to the workstation. When the position sensor is in the magnetic field, the location of the position sensor can be mathematically determined relative to the electromagnetic field source (e.g., the operating table and/or the electromagnetic generator). The workstation and the control unit may communicate to determine the position of the position sensor relative to the patient.

Figure 2:
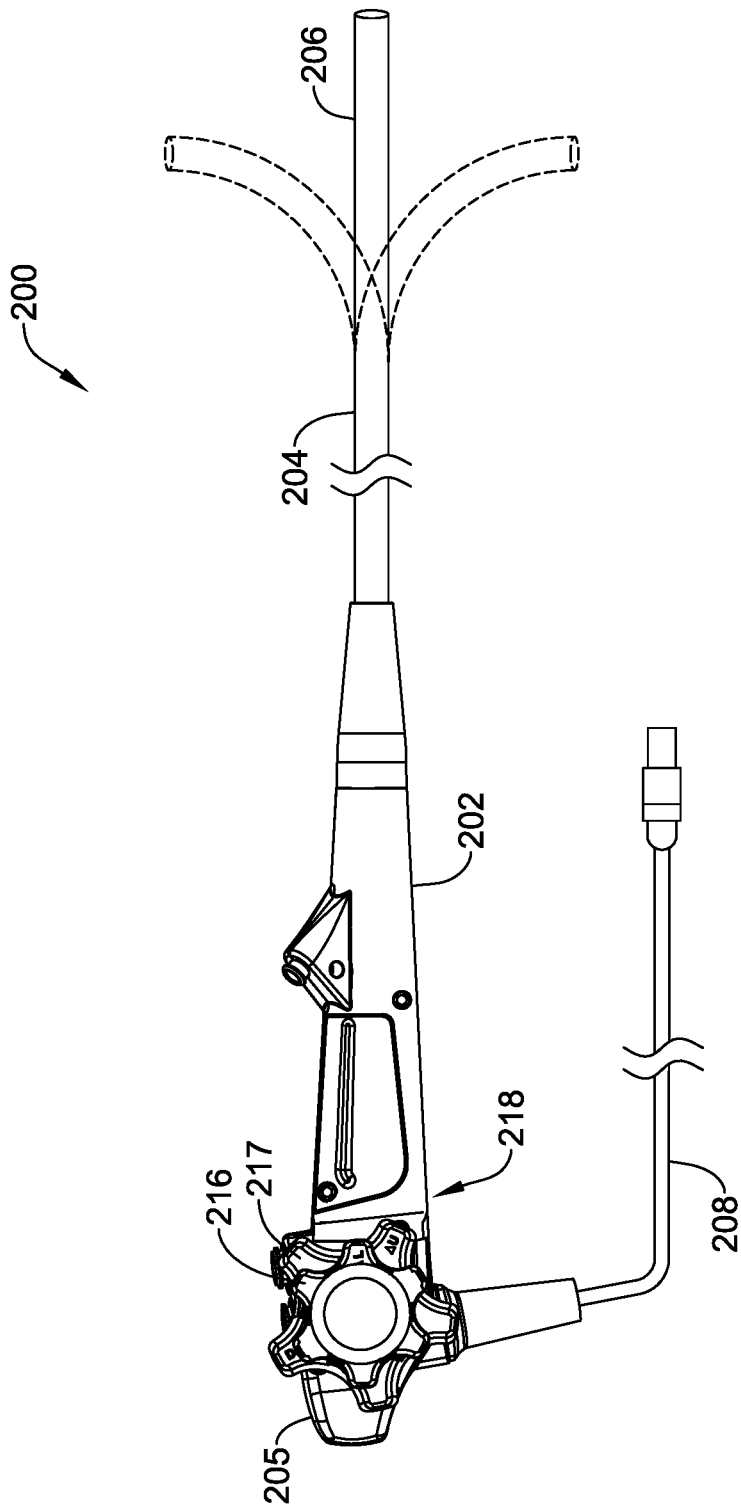
FIG. 2 is a schematic illustration of selected aspects of an endoscopic system.

FIG. 2 illustrates selected aspects of an alternative endoscopic system that may be used in conjunction with other aspects of the disclosure. In some embodiments, the endoscopic system may include an endoscope 200. The endoscope 200 may be specific to a particular endoscopic procedure, such as, e.g., ureteroscopy, or may be a general-purpose device suitable for a wide variety of procedures. In some embodiments, the endoscope 200 includes a handle 202 and an elongate shaft 204 extending distally therefrom, wherein the handle 202 includes a first non-motorized and non-ratcheting mechanism configured to articulate a distal tip portion 206 of the elongate shaft 204 in a first plane and a second non-motorized and non-ratcheting mechanism configured to articulate the distal tip portion 206 of the elongate shaft 204 in a second plane different from the first plane. In some embodiments, the first plane may be oriented at a non-zero angle to the second plane. In some embodiments, the first plane may be oriented perpendicular to the second plane. Other configurations are also contemplated.

In some embodiments, the distal tip portion 206 may include a camera and may, for example, have deflection and/or articulation capabilities in one or more directions for viewing patient anatomy. In some embodiments, the endoscope 200 may be a duodenoscope such as an Exalt™ Model D scope. However, other medical devices, such as another endoscope or related system, (e.g., SpyScope™ DS, SpyGlass™ DS, etc.) may be used in addition to or in place of a duodenoscope. In some embodiments, the endoscope 200 may be configured to deliver fluid from a fluid management system to a treatment site via the elongate shaft 204. The elongate shaft 204 may include one or more working lumens for receiving a flow of fluid and/or other medical devices therethrough. In some embodiments, the endoscope 200 may be connected to the fluid management system via one or more supply line(s).

In some embodiments, the handle 202 of the endoscope 200 may include a plurality of elements configured to facilitate the endoscopic procedure. In some embodiments, a cable 208 extends from the handle 202 and is configured for attachment to an electronic device (not pictured) such as e.g. a computer system, a console, a microcontroller, etc. for providing power, analyzing endoscopic data, controlling the endoscopic intervention, or performing other functions. In some embodiments, the electronic device to which the cable 208 is connected may have functionality for recognizing and exchanging data with other endoscopic accessories. The handle 202 may include a grip area 218 for the operating physician to grasp while performing the endoscopic procedure.

In some embodiments, the handle 202 and/or the first non-motorized and non-ratcheting mechanism may include a first actuator 216 disposed on an exterior of the handle 202 at a proximal end 205 of the handle 202, wherein the first actuator 216 may be actuated to control articulation of the distal tip portion 206 in the first plane. In some embodiments, the handle 202 and/or the second non-motorized and non-ratcheting mechanism may include a second actuator 217 disposed on an exterior of the handle 202 at a proximal end 205 of the handle 202, wherein the second actuator 217 may be actuated to control articulation of the distal tip portion 206 in the second plane. In some embodiments, the first actuator 216 may be movably coupled to the handle 202. In some embodiments, the first actuator 216 may be configured to engage with and/or actuate the first non-motorized and non-ratcheting mechanism. In some embodiments, the second actuator 217 may be movably coupled to the handle 202. In some embodiments, the second actuator 217 may be configured to engage with and/or actuate the second non-motorized and non-ratcheting mechanism.

In some embodiments, the distal tip portion 206 may be articulatable in response to a manually applied force exerted upon the handle 202 and/or elements thereof (e.g., the first actuator 216, the second actuator 217, etc.) as described herein. In one example, the first actuator 216 may include a first lever configured to articulate the distal tip portion 206 of the endoscope 200 in the first plane and the second actuator 217 may include a second lever configured to articulate the distal tip portion 206 of the endoscope 200 in the second plane. In another example, the first actuator 216 may include a first rotatable knob configured to articulate the distal tip portion 206 of the endoscope 200 in the first plane and the second actuator 217 may include a second rotatable knob configured to articulate the distal tip portion 206 of the endoscope 200 in the second plane. Other configurations are also contemplated.

In some embodiments, the endoscope 200 may include a first pulley or rotating member disposed within the handle 202 and operatively connected to the distal tip portion 206. In some embodiments, one or more first cables, wires, or other filaments may be engaged with and/or connected to the first pulley within the handle 202. In some embodiments, the one or more first cables, wires, or filaments may be engaged with and/or connected to the distal tip portion 206, such that tension applied to the one or more first cables, wires, or filaments by the first pulley moves and/or articulates the distal tip portion 206 in the first plane. In some embodiments, the endoscope 200 may include a second pulley or rotating member disposed within the handle 202 and operatively connected to the distal tip portion 206. In some embodiments, one or more second cables, wires, or other filaments may be engaged with and/or connected to the second pulley within the handle 202. In some embodiments, the one or more second cables, wires, or filaments may be engaged with and/or connected to the distal tip portion 206, such that tension applied to the one or more second cables, wires, or filaments by the second pulley moves and/or articulates the distal tip portion 206 in the second plane.

In some embodiments, the endoscope 200 may be in electronic communication with a workstation via a wired connection (e.g., the cable 208). In some embodiments, the workstation may include a touch panel computer, an interface box for receiving the wired connection (e.g., the cable 208), a cart, and a power supply, among other features. In some embodiments, the interface box may be configured with a wired or wireless communication connection with the controller of the fluid management system. The touch panel computer may include at least a display screen and an image processor. In some embodiments, the workstation may be a multi-use component (e.g., used for more than one procedure) while the endoscope 200 may be a single use device, although this is not required. In some embodiments, the workstation may be omitted and the endoscope 200 may be electronically coupled directly to the controller of the fluid management system.

In some embodiments, the endoscope 200 may include one or more sensors proximate the distal tip portion 206 and/or the distal end of the elongate shaft 204. For example, the endoscope 200 may include a pressure sensor at the distal tip portion 206 of the elongate shaft 204 to measure intracavity pressure within the treatment site. The endoscope 200 may also include other sensors such as, for example, a temperature sensor, a Fiber Bragg grating optical fiber to detect stresses, and/or an antenna or electromagnetic sensor (e.g., a position sensor). In some embodiments, the distal tip portion 206 and/or the distal end of the endoscope 200 may also include at least one camera to provide a visual feed to the user on the display screen of the touch panel computer. In another embodiment, the endoscope 200 may include two cameras having different communications requirements or protocols so that different information may be relayed to the user by each camera. When so provided, the user may switch back and forth between the cameras at will through the touch screen interface and/or the touch panel computer. While not explicitly shown, the elongate shaft 204 may include one or more working lumens for receiving the fluid and/or other medical devices.

In some embodiments, the location of the distal tip portion 206 and/or the distal end of the elongate shaft 204 may be tracked during use. For example, a mapping and navigation system may include an operating table (or other procedural or examination table or chair, etc.) configured to act or function as an electromagnetic generator to generate a magnetic field of a known geometry. Alternatively, or additionally, an electromagnetic generator separate from the operating table may be provided. The operating table and/or the electromagnetic generator may be coupled to a control unit which may include among other features, a processor, a memory, a display, and an input means. A position sensor (e.g., the electromagnetic sensor, etc.) or antenna, may be incorporated into the distal tip portion 206 and/or the distal end of the elongate shaft 204 of the endoscope 200. The position sensor may be configured for use in sensing a location of the position sensor in the magnetic field of the mapping and navigation system. In some embodiments, the position sensor may be electronically coupled to the workstation. When the position sensor is in the magnetic field, the location of the position sensor can be mathematically determined relative to the electromagnetic field source (e.g., the operating table and/or the electromagnetic generator). The workstation and the control unit may communicate to determine the position of the position sensor relative to the patient.

Figure 3:
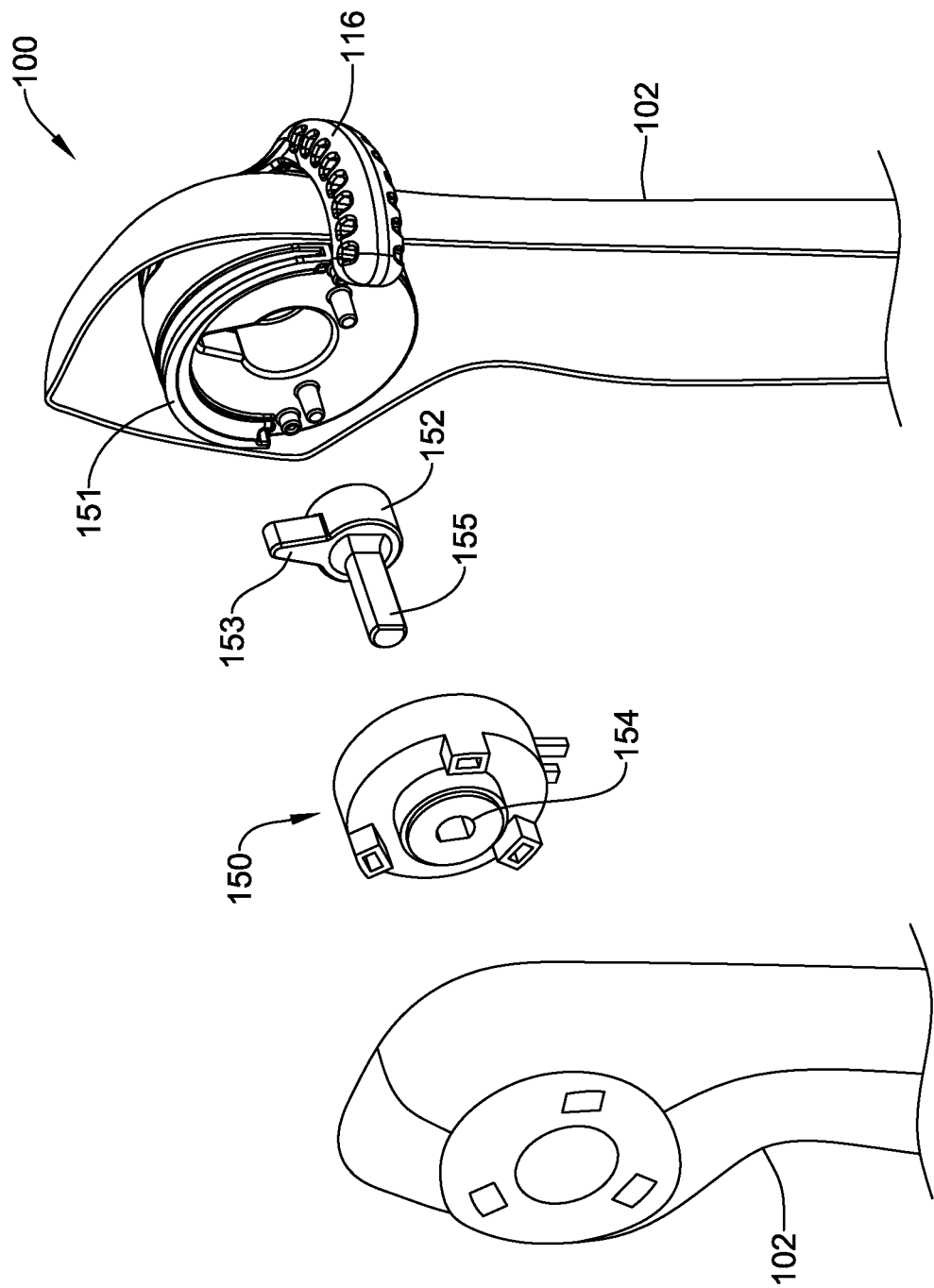
FIGS. 3-4 illustrate selected aspects of a clutch mechanism in the endoscopic system of FIGS. 1A-1B.

FIG. 3 illustrates a partially exploded view of selected features of the endoscope 100 in conjunction with selected features of the disclosure. In some embodiments, the non-motorized and non-ratcheting mechanism of the endoscope 100 may include a clutch mechanism 150 actuatable in response to an electrical signal. In some embodiments, the clutch mechanism 150 may be disposed within the handle 102 of the endoscope 100 adjacent and/or proximate the actuator 116. In some embodiments, the clutch mechanism 150 may include a coupler 152 configured to engage a rotor shaft 154 of the clutch mechanism 150 to a pulley 151 disposed within the handle 102. In some embodiments, the coupler 152 may be non-rotatably engaged with the pulley 151. In some embodiments, the coupler 152 may include a key 153 configured to engage with the pulley 151. In some embodiments, the coupler 152 may be removably engaged with the pulley 151, as shown in FIG. 3. In some embodiments, the coupler 152 may be fixedly attached to and/or integrally formed with the pulley 151. In some embodiments, the coupler 152 may be non-rotatably engaged with the rotor shaft 154. In some embodiments, the coupler 152 may include a D-shaped shaft 155 configured to engage with and/or be received by the rotor shaft 154. In some embodiments, the coupler may be slidably and/or removably engaged with the rotor shaft 154. In some embodiments, the clutch mechanism 150 may be operatively and/or electrically connected to a power source. In some embodiments, the power source may be and/or may be disposed within the endoscope 100. In some embodiments, the power source may be a battery disposed within and/or coupled to the clutch mechanism 150. The power source may be configured to selectively provide/interrupt the electrical signal to the clutch mechanism 150 and/or the power source may be configured to selectively adjust/change the electrical signal level to the cutch mechanism 150. In some embodiments, similar features may also apply to and/or be associated with the endoscope 200 and/or the clutch mechanism(s) associated therewith.

Figure 4:
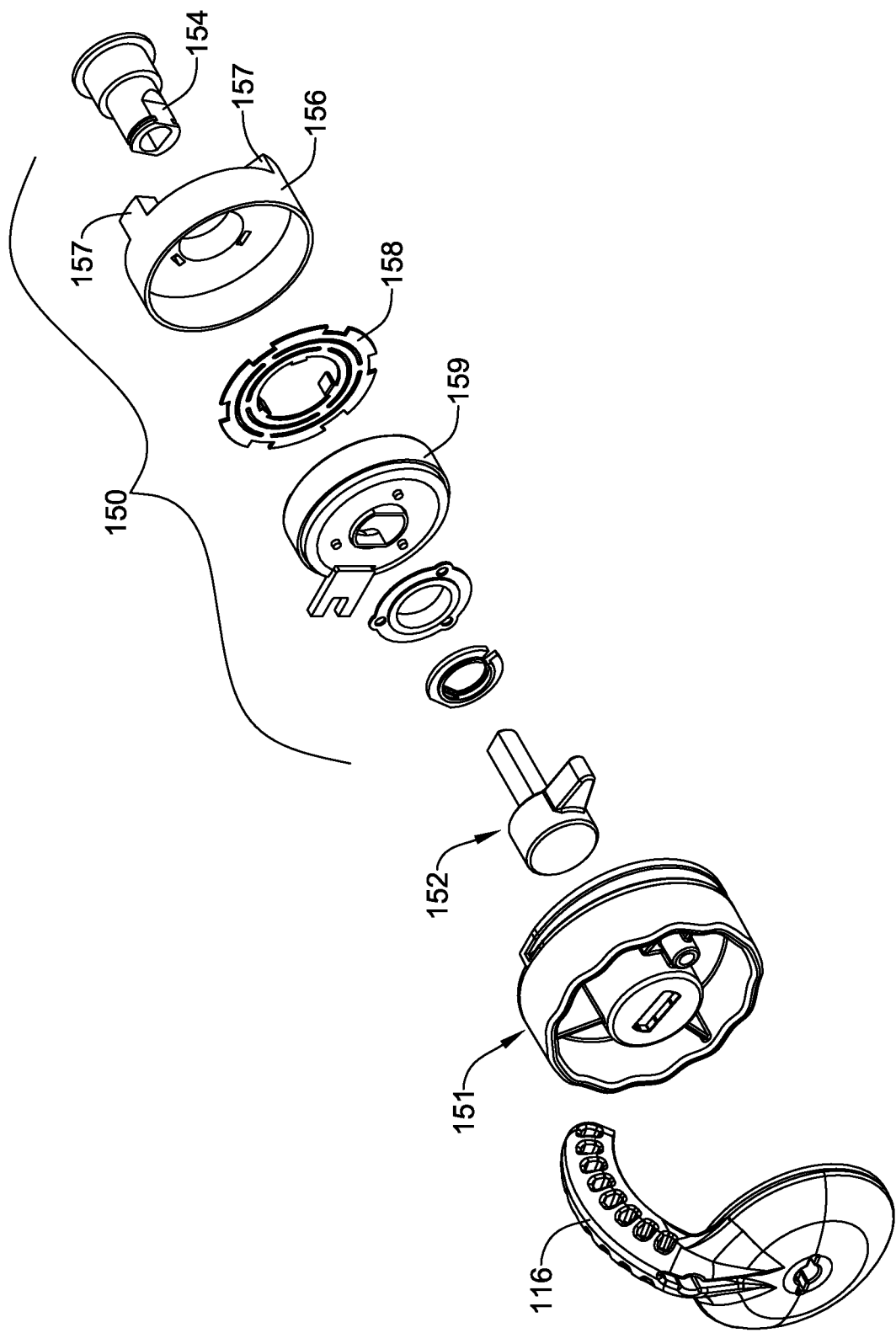

FIG. 4 is a partially exploded view showing selected features and/or components of the clutch mechanism 150. In some embodiments, the clutch mechanism 150 may include a clutch housing 156 configured to non-rotatably couple the clutch mechanism 150 to the handle 102. For example, the clutch housing 156 may include one or more protrusions 157 configured to engage corresponding apertures and/or receiving features formed in the handle 102, as seen in FIG. 3. An armature 158 and a rotor 159 may be disposed within the clutch housing 156. The armature 158 may include one or more projections non-rotatably engaged with one or more corresponding recesses in the clutch housing 156. The rotor 159 may be configured to rotate freely with respect to the armature 158 and/or the clutch housing 156 in the absence of the electrical signal and/or when the clutch mechanism 150 fails to receive the electrical signal. Conversely, the rotor 159 may be configured to lock to and/or relative to the armature 158 when the electrical signal is received by the clutch mechanism 150 (e.g., when the clutch mechanism 150 is activated or engaged) to prevent rotation of the rotor 159. In at least some embodiments, when the electrical signal is received by the clutch mechanism 150, the rotor 159 becomes energized and develops a magnetic attraction to the armature 158. When the rotor 159 engages the armature 158, the rotor shaft 154 is prevented from rotating, which in turn prevents rotation of the coupler 152 and locks the pulley 151 in its then-current position. As such, the clutch mechanism 150 is configured to prevent articulation of the distal tip portion 106 when the electrical signal is received by the clutch mechanism 150, thereby effectively locking the distal tip portion 106 in its then-current configuration and/or position.

In some embodiments, the clutch mechanism 150 may be configured to operate and/or function in an inverse manner to that described above. For example, in some embodiments, the rotor 159 may be configured to lock to and/or relative to the armature 158 in the absence of the electrical signal and/or when the clutch mechanism 150 fails to receive the electrical signal. As such, the clutch mechanism 150 may be configured to prevent articulation of the distal tip portion 106 when no electrical signal is received by the clutch mechanism 150, thereby locking the distal tip portion 106 in its then-current configuration and/or position. In some embodiments, when the electrical signal is received by the clutch mechanism 150, the rotor 159 becomes de-energized (and/or a magnetic polarity of the rotor 159 is reversed) and magnetic attraction to the armature 158 is terminated to release the clutch mechanism 150 and allow articulation of the distal tip portion 106. Accordingly, the rotor 159 may be configured to rotate freely with respect to the armature 158 and/or the clutch housing 156 when the electrical signal is received by the clutch mechanism 150, thereby permitting and/or enabling movement of the distal tip portion 106.

Figure 5:
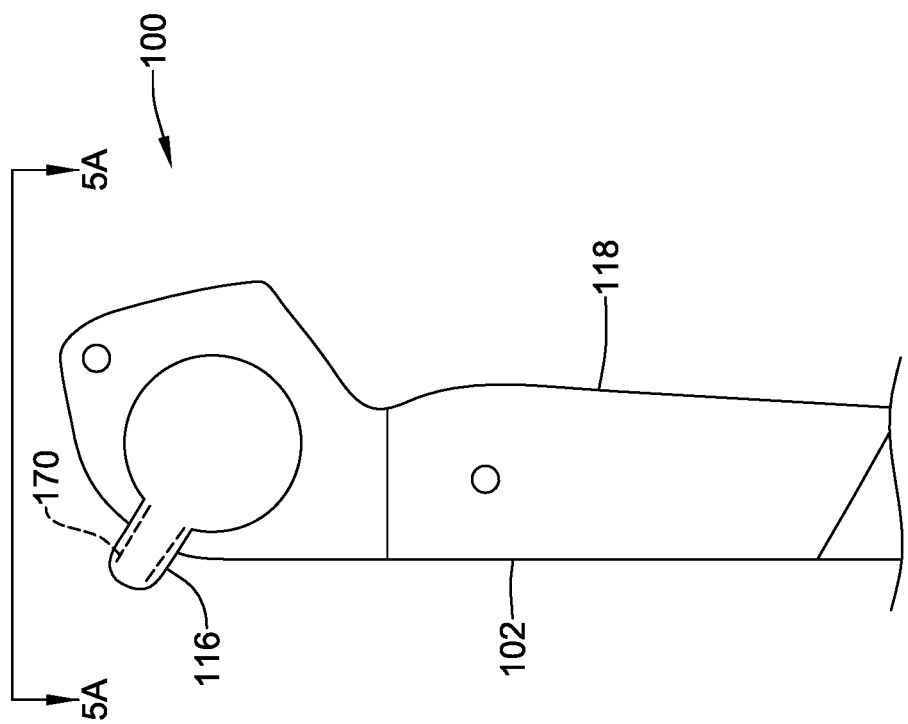
FIG. 5 illustrates selected aspects of a clutch mechanism in the endoscopic system of FIGS. 1A-1B.

FIG. 5 illustrates an example configuration of the endoscope 100. In FIG. 5, no force is being applied to the actuator 116 by the physician's hand and/or the physician's thumb (e.g., the manually applied force is not being exerted upon the handle 102 and/or the actuator 116). In some embodiments, the non-motorized and non-ratcheting mechanism of the endoscope 100 may include a strain gauge 170 and a logic controller (e.g., a microcontroller, a circuit board, a comparator circuit, etc.; not shown) configured to detect the manually applied force using the strain gauge 170. The logic controller may be configured to actuate, send, terminate, and/or otherwise manipulate the electrical signal being sent to and/or received by the clutch mechanism 150 in response to a detected strain or lack thereof. In some embodiments, the strain gauge 170 may include one or more strain gauges, at least one strain gauge, and/or a plurality of strain gauges. In some embodiments, the strain gauge 170 may include two to four strain gauges (or another suitable number) working together in a bridge configuration. Other configurations are also contemplated. In some embodiments, the actuator 116 may include the strain gauge 170, as shown in FIG. 5 for example. In an alternative configuration, the strain gauge 170 may be attached to, disposed on, and/or may be a part of a shaft that is configured to couple the actuator 116 to the pulley 151. In another alternative configuration, the strain gauge 170 may be attached to, disposed on, and/or may be a part of the pulley 151 and/or a portion of the pulley 151 that is attached to and/or engaged with the actuator 116. For example, the shaft may be configured to transfer the manually applied force from the actuator 116 to the pulley 151. In some embodiments, the absence of the manually applied force may generate and/or send the electrical signal to the clutch mechanism 150 to therefore lock the distal tip portion 106 in its then-current configuration and/or position and additionally prevent articulation of the distal tip portion 106 away from its then-current configuration. In some embodiments, the strain gauge 170 may be and/or may take the form of a resistive strain gauge. In some embodiments, the strain gauge 170 may be and/or may take the form of another type of sensor, such as but not limited to resistive force sensors, load cells, capacitive sensors, etc.

Figure 5A:
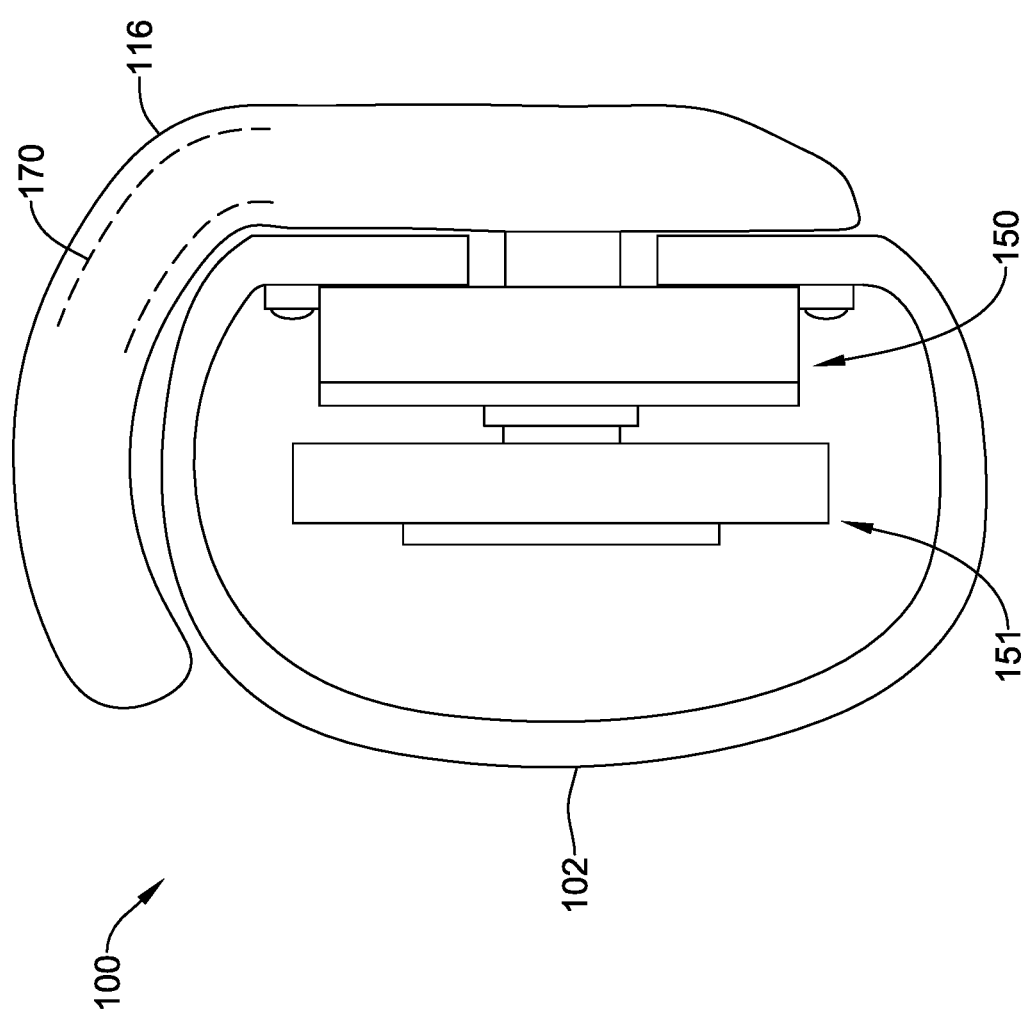
FIG. 5A is a partial cutaway end view of the endoscopic system of FIG. 5.

FIG. 5A is a partial cutaway end view of FIG. 5 illustrating an example configuration of selected internal components of the endoscope 100 and the clutch mechanism 150. In some embodiments, when the manually applied force is not being applied to the handle 102 and/or the actuator 116, the electrical signal is sent to the clutch mechanism 150, thereby engaging and/or activating the clutch mechanism 150, as shown in FIG. 5A, to prevent rotation and/or movement of the pulley 151 relative to the handle 102 and thereby further prevent articulation of the distal tip portion 106. In the example of FIGS. 5 and 5A, when the strain gauge 170 fails to detect the manually applied force exerted upon the handle 102 and/or the actuator 116, the logic controller may understand this to represent an intent of the physician to lock the distal tip portion 106 in its then-current configuration and/or position, and/or an intent to prevent further articulation of the distal tip portion 106 away from its then-current configuration. It will be understood that the configuration shown in FIG. 5A is merely representative, and selected components may be re-arranged as needed to accommodate packaging and/or space requirements. For example, in FIG. 5A, the clutch mechanism 150 is shown disposed within the handle 102 between the pulley 151 and the actuator 116, but in at least some embodiments, the clutch mechanism 150 may be disposed within the handle 102 on an opposite side of the pulley 151 from the actuator 116, as generally shown in FIG. 3.

FIGS. 6A and 6B are graphs illustrating a relationship between a detected strain and the electrical signal being sent to the clutch mechanism 150 in the configuration shown in FIGS. 5 and 5A. As may be seen in the graphs, as no strain is detected over time, within a predetermined range, band, and/or deviation, the electrical signal (e.g., voltage) sent to and/or received by the clutch mechanism 150 remains generally constant at a predetermined value V. The predetermined range, band, and/or deviation for registering strain on the strain gauge 170 may be within plus or minus 5.0%, 3.0%, 2.5%, 2.0%, 1.0%, 0.5%, etc. of a desired or expected value. Within the predetermined range, band, and/or deviation, the logic controller may register no change in strain. As such, the correlation between the lack of strain detected using the strain gauge 170 and the electrical signal may be easily visualized. In this configuration, the clutch mechanism 150 is engaged and/or activated and the actuator 116 and/or the pulley 151 is locked in position and/or prevented from moving. Although shown as providing an electrical signal greater than zero in the locked position in which no strain is detected, in other embodiments, the electrical signal sent to/or received by the clutch mechanism 150 may be zero in the locked position in which no strain is detected.

FIG. 7 illustrates an example configuration of the endoscope 100 of FIG. 5. In FIG. 7, the manually applied force F is being exerted upon the handle 102 and/or the actuator 116 by the physician's hand and/or the physician's thumb. The strain gauge 170 may be configured to detect the manually applied force F exerted upon the handle 102 and/or the actuator 116. The electrical signal being sent to the clutch mechanism 150 may be interrupted in response to a strain detected using the strain gauge 170. As such, the clutch mechanism 150 may be released and/or deactivated when the strain gauge 170 detects the manually applied force F above a threshold amount, thereby permitting articulation of the distal tip portion 106. In an alternative configuration, the electrical signal may be sent and/or applied to the clutch mechanism 150 in response to a strain detected using the strain gauge 170, and the electrical signal may release the clutch mechanism 150.

Figure 7A:
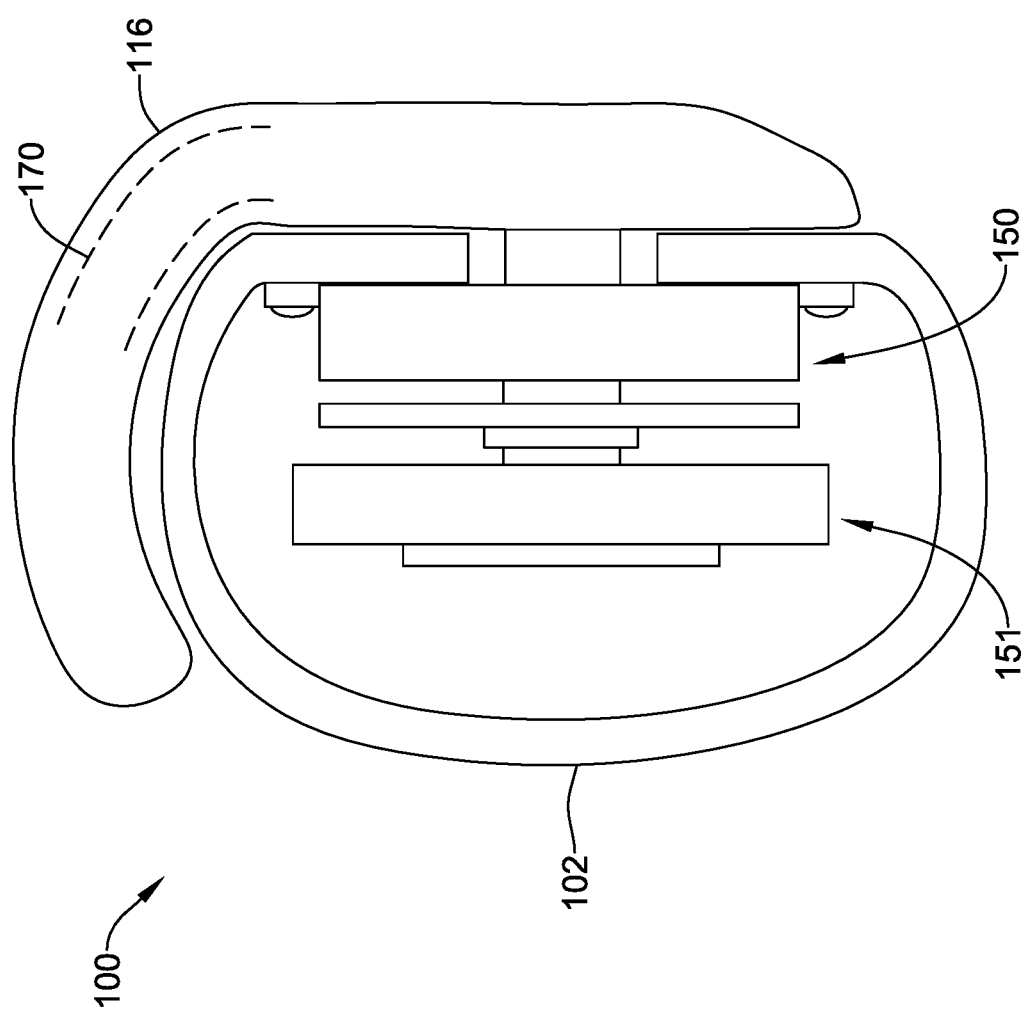
FIG. 7A is a partial cutaway end view of the endoscopic system of FIG. 7.

FIG. 7A is a partial cutaway end view of FIG. 7 illustrating an example configuration of selected internal components of the endoscope 100 and the clutch mechanism 150. In some embodiments, when the manually applied force is being applied to the handle 102 and/or the actuator 116, the electrical signal being sent to the clutch mechanism 150 changes, (e.g., is interrupted), thereby releasing and/or deactivating the clutch mechanism 150, as shown in FIG. 7A, to permit rotation and/or movement of the pulley 151 relative to the handle 102 and thereby permit articulation of the distal tip portion 106. In the example of FIGS. 7 and 7A, when the strain gauge 170 detects the manually applied force F exerted upon the handle 102 and/or the actuator 116 above a threshold amount, the logic controller (e.g., a circuit board, for example) may understand this to represent an intent of the physician to move and/or articulate the distal tip portion 106 from its then-current configuration and/or position, and/or an intent to further move and/or articulate the distal tip portion 106. It will be understood that the configuration shown in FIG. 7A is merely representative, and selected components may be re-arranged as needed to accommodate packaging and/or space requirements. For example, in FIG. 7A, the clutch mechanism 150 is shown disposed within the handle 102 between the pulley 151 and the actuator 116, but in at least some embodiments, the clutch mechanism 150 may be disposed within the handle 102 on an opposite side of the pulley 151 from the actuator 116, as generally shown in FIG. 3.

FIGS. 8A and 8B are graphs illustrating a relationship between a detected strain and the electrical signal being sent to the clutch mechanism 150 in the configuration shown in FIGS. 7 and 7A. As may be seen in the graphs, as strain is detected over time, within a predetermined range, band, and/or deviation, the electrical signal (e.g., voltage) sent to and/or received by the clutch mechanism 150 is interrupted and drops from the predetermined value V toward and/or to zero. The predetermined range, band, and/or deviation for registering strain on the strain gauge 170 may be within plus or minus 5.0%, 3.0%, 2.5%, 2.0%, 1.0%, 0.5%, etc. of a desired or expected value. Within the predetermined range, band, and/or deviation, the logic controller may register no change in strain. As such, the correlation between the strain detected using the strain gauge 170 and the electrical signal may be easily visualized. Although shown as dropping the electrical signal to zero when a strain above a threshold amount is detected, in other embodiments, when the detected strain increases above a threshold amount, the electrical signal sent to/or received by the clutch mechanism 150 may change (e.g., increase or decrease) from the electrical signal provided when in the locked position and no strain is detected. The change in electrical signal may release the clutch mechanism 150, allowing for deflection of the distal tip portion 106.

Figure 9A:
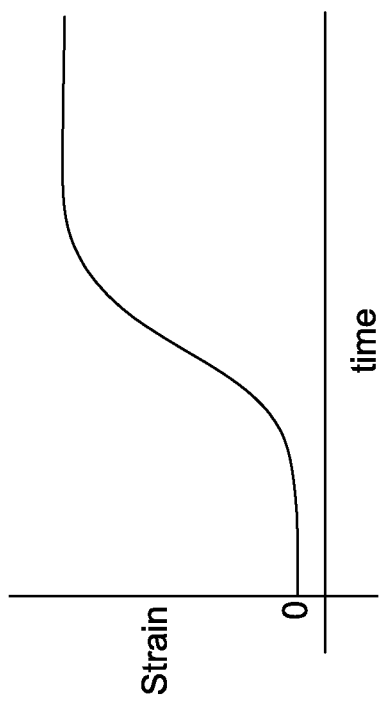
FIGS. 9A-9B are graphs illustrating interactions between different characteristics of the clutch mechanism of FIGS. 7-7A.
Figure 9B:
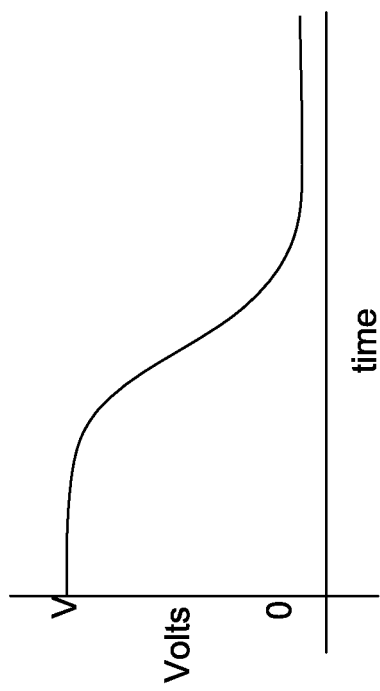

FIGS. 9A and 9B are graphs illustrating an alternate relationship between a detected strain and the electrical signal being sent to the clutch mechanism 150 in the configuration shown in FIGS. 7 and 7A. As may be seen in the graphs, as strain is gradually increased and/or detected over time, the electrical signal (e.g., voltage) sent to and/or received by the clutch mechanism 150 may be gradually reduced from the predetermined value V toward and/or to zero. As in the above examples, a predetermined range, band, and/or deviation for registering strain on the strain gauge 170 may be within plus or minus 5.0%, 3.0%, 2.5%, 2.0%, 1.0%, 0.5%, etc. of a desired or expected value. Within the predetermined range, band, and/or deviation, the logic controller may register no change in strain. As such, the correlation between the strain detected using the strain gauge 170 and the electrical signal may be easily visualized. A gradual increase in strain and/or a gradual change (e.g., reduction) in the electrical signal (e.g., voltage) sent to and/or received by the clutch mechanism 150 may produce, cause, and/or correlate to a gradual release by the clutch mechanism 150 such that resistance to movement and/or articulation of the distal tip portion 106 is also gradually reduced and/or released. In this alternate relationship, the clutch mechanism 150 may act as a braking mechanism, wherein a higher strain detected and/or more manually applied force F indicates an intent to move and/or articulate the distal tip portion 106 further and/or faster than a lower strain detected and/or less manually applied force F. However, as above, when the manually applied force F is released and/or removed, the clutch mechanism 150 may immediately lock the distal tip portion 106 in its then-current configuration and/or position and thereby prevent further movement and/or articulation of the distal tip portion 106. As discussed above, although shown as gradually dropping the electrical signal to zero as a gradual change (e.g., increase) in strain is detected, in other embodiments, when the detected strain increases, the electrical signal sent to/or received by the clutch mechanism 150 may gradually change (e.g., increase or decrease) from the electrical signal provided when in the locked position and no strain is detected. The gradual change in electrical signal may release the clutch mechanism 150, allowing for deflection of the distal tip portion 106.

Figure 10:
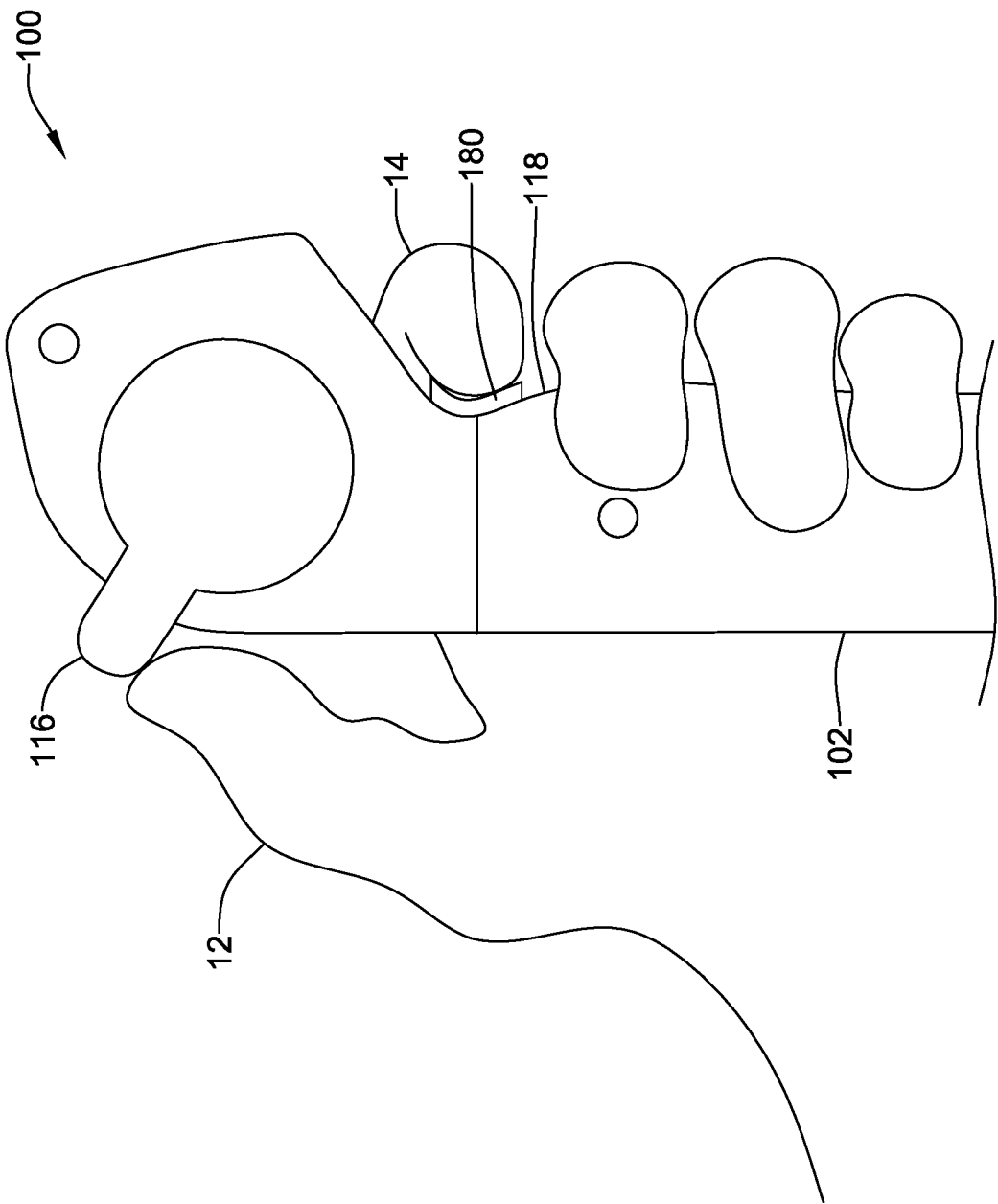
FIGS. 10-11 illustrate selected aspects of an alternative configuration of a clutch mechanism in the endoscopic system of FIGS. 1A-1B.
Figure 11:
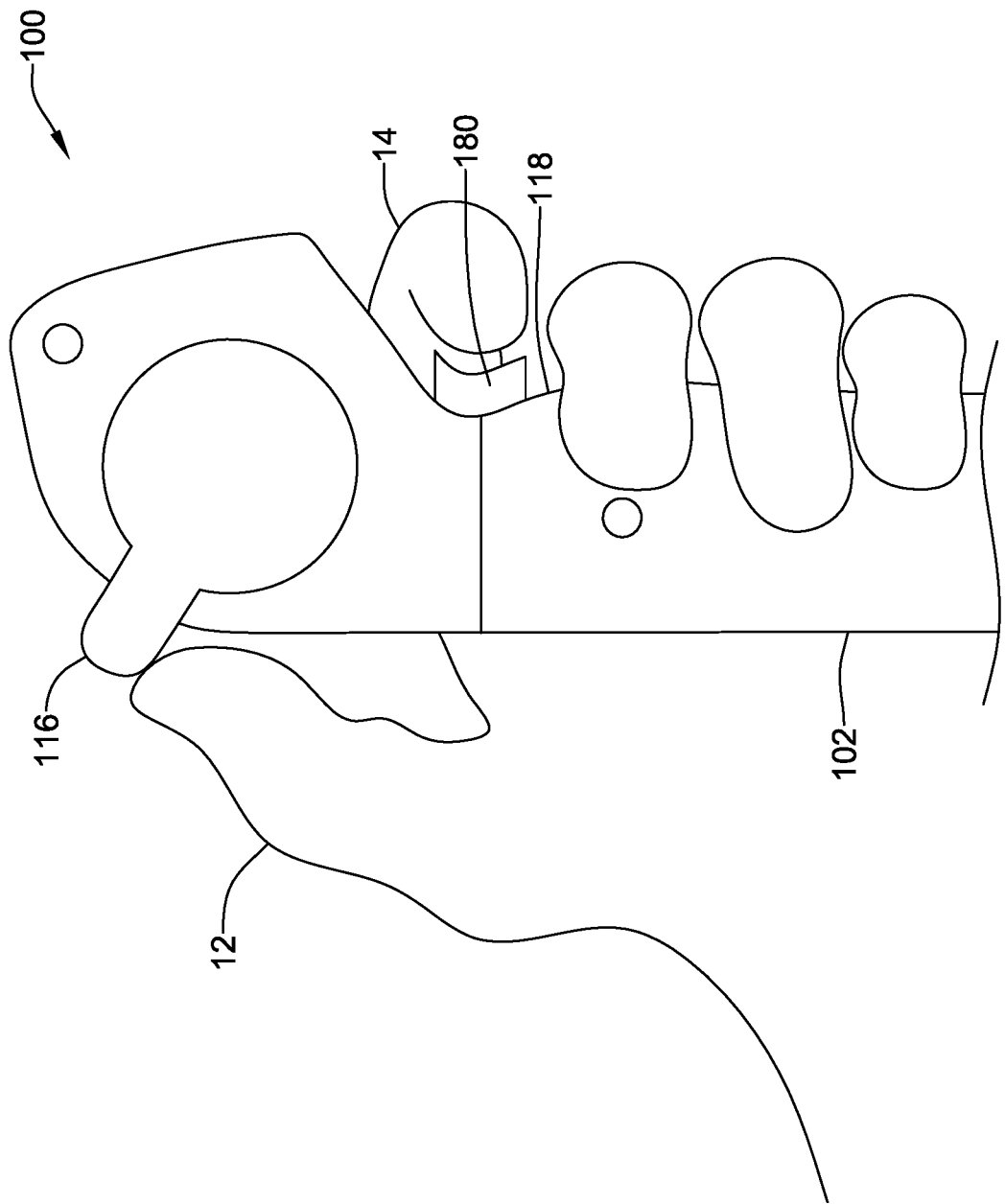

FIGS. 10 and 11 illustrate another example configuration of the endoscope 100. In some embodiments, the endoscope 100 may include an actuatable button 180 disposed on, formed in, and/or extending through the handle 102. In some embodiments, the actuatable button 180 may include one or more actuatable buttons, at least one actuatable button, and/or a plurality of actuatable buttons. In some embodiments, the actuatable button 180 may be configured to interrupt the electrical signal (e.g., voltage) being sent to the clutch mechanism 150 when the actuatable button 180 is in a depressed position, as seen in FIG. 10, and the electrical signal (e.g., voltage) may be sent to and/or received by the clutch mechanism 150 when the actuatable button 180 is in a released position, as seen in FIG. 11.

In FIGS. 10 and 11, the actuatable button 180 is configured as a trigger to be actuated by the physician's finger 14 while the actuator 116 is configured to be actuated and/or moved by the physician's thumb 12. Other configurations are also contemplated. A position of the actuatable button 180 may function similar to and/or in the same manner as the strain gauge 170 described above. Alternatively, a strain gauge may be included in and/or on the actuatable button 180 in a manner similar to the strain gauge 170 described above. For example, in some embodiments, when the actuatable button 180 is in the released position (e.g., zero strain on the actuatable button 180), the electrical signal may be generated and/or sent to the clutch mechanism 150 to therefore lock the distal tip portion 106 in its then-current configuration and/or position and additionally prevent movement and/or articulation of the distal tip portion 106. The graphs shown in FIGS. 6A and 6B apply in a similar manner to the configuration of FIGS. 10 and 11, wherein the left side of the graph on FIG. 6A would correspond to the position of the actuatable button 180 (or the strain on the actuation button 180). The graphs shown in FIGS. 6A and 6B correspond to the actuatable button 180 being in the released position of FIG. 11 (e.g., zero strain on the actuatable button 180), wherein the electrical signal (e.g., voltage) is being sent to the clutch mechanism 150 at the predetermined value V to engage the clutch mechanism 150 and/or to lock the distal tip portion 106 in its then-current configuration and/or position and additionally prevent movement and/or articulation of the distal tip portion 106. The other graphs described above may also be correlated to the configuration of FIGS. 10 and 11. For example, in some embodiments, when the actuatable button 180 is in the depressed position (e.g., strain on the actuatable button 180), the electrical signal may be interrupted to therefore release the clutch mechanism 150 and/or permit movement and/or articulation of the distal tip portion 106. The graphs shown in FIGS. 8A and 8B may apply in a similar manner to the configuration of FIGS. 10 and 11, wherein the left side of the graph on FIG. 8A would correspond to the position of the actuatable button 180 (or the strain on the actuation button 180). The graphs shown in FIGS. 8A and 8B correspond to the actuatable button 180 being shifted and/or actuated from the released position of FIG. 10 (e.g., no strain on the actuatable button 180) to the depressed position of FIG. 11 (e.g., strain on the actuatable button 180), wherein the electrical signal (e.g., voltage) to the clutch mechanism 150 is changed, such as being interrupted and/or no electrical signal (e.g., voltage) is being received by the clutch mechanism 150 when the actuatable button 180 is in the depressed position.

Additionally, the graphs shown in FIGS. 9A and 9B may apply in a similar manner to the configuration of FIGS. 10 and 11, wherein the left side of the graph on FIG. 8A would correspond to the position of the actuatable button 180 (or the strain on the actuation button 180). The graphs shown in FIGS. 9A and 9B may correspond to the actuatable button 180 being gradually moved from the released position toward and/or to depressed position of FIG. 11 (e.g., strain on the actuatable button 180), wherein the electrical signal (e.g., voltage) to the clutch mechanism 150 is being gradually changed, such as gradually interrupted. As may be seen in the graphs, as the position of the actuatable button 180 moves toward the depressed position (e.g., strain is gradually increased and/or detected over time), the electrical signal (e.g., voltage) sent to and/or received by the clutch mechanism 150 may be gradually changed, such as gradually reduced from the predetermined value V toward and/or to zero. As such, the correlation between the position of the actuatable button 180 and the electrical signal may be easily visualized. A gradual change in position of the actuatable button 180 (e.g., a gradual increase in strain) and/or a gradual change (e.g., decrease or increase) in the electrical signal (e.g., voltage) sent to and/or received by the clutch mechanism 150 may produce, cause, and/or correlate to a gradual release by the clutch mechanism 150 such that resistance to movement and/or articulation of the distal tip portion 106 is also gradually reduced and/or released. In this alternate relationship, the clutch mechanism 150 may act as a braking mechanism similar to the configuration(s) described above.

Figure 12:
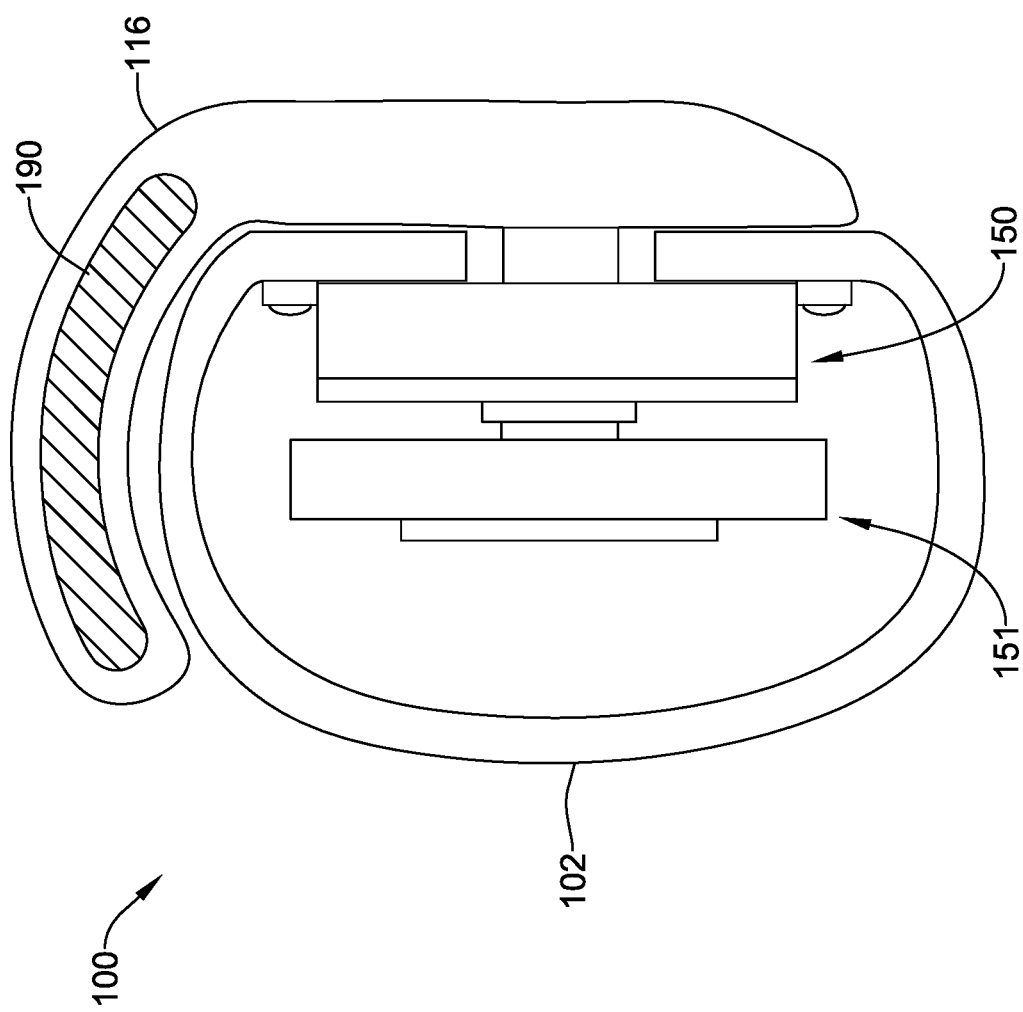
FIG. 12 illustrates selected aspects of an alternative configuration of a clutch mechanism in the endoscopic system of FIGS. 1A-1B.

FIG. 12 is a partial cutaway end view illustrating another example configuration of the endoscope 100. In the example of FIG. 12, the endoscope 100 may include a touch sensor 190. In some embodiments, the non-motorized and non-ratcheting mechanism of the endoscope 100 may include the touch sensor 190 configured to detect a user or a physician's hand in contact with the non-motorized and non-ratcheting mechanism. In some embodiments, the touch sensor 190 may be configured to detect the physician's thumb in contact with the actuator 116. In some embodiments, the touch sensor 190 may include a touch-sensitive resistive strip disposed on an outer surface of the actuator 116. In some embodiments, the touch sensor 190 may include one or more touch sensors, at least one touch sensor, and/or a plurality of touch sensors. In some embodiments, the actuator 116 may include the touch sensor 190 disposed thereon, as shown in FIG. 12 for example. In some embodiments, the touch sensor 190 may be configured to interrupt the electrical signal (e.g., voltage) being sent to the clutch mechanism 150 when the touch sensor 190 detects the physician's hand and/or the physician's thumb in contact with the handle 102, the actuator 116, and/or the non-motorized and non-ratcheting mechanism, and the electrical signal (e.g., voltage) may be sent to the clutch mechanism 150 when the touch sensor 190 fails to detect the physician's hand and/or the physician's thumb in contact with the handle 102, the actuator 116, and/or the non-motorized and non-ratcheting mechanism.

In some embodiments, the touch sensor 190 may function similar to and/or in the same manner as the actuatable button 180 described above. For example, in some embodiments, when the touch sensor 190 fails to detect the physician's hand and/or the physician's thumb in contact with the handle 102, the actuator 116, and/or the non-motorized and non-ratcheting mechanism, the electrical signal may be generated and/or sent to the clutch mechanism 150 to therefore lock the distal tip portion 106 in its then-current configuration and/or position and additionally prevent movement and/or articulation of the distal tip portion 106. The graphs shown in FIGS. 6A and 6B apply in a similar manner to the configuration of FIG. 12, wherein the left side of the graph on FIG. 6A would correspond to the touch sensor 190 failing to detect the physician's hand and/or the physician's thumb in contact with the handle 102, the actuator 116, and/or the non-motorized and non-ratcheting mechanism. The graphs shown in FIGS. 6A and 6B correspond to the physician's hand and/or the physician's thumb not being in contact with the touch sensor 190, wherein the electrical signal (e.g., voltage) is being sent to the clutch mechanism 150 at the predetermined value V to engage the clutch mechanism 150 and/or to lock the distal tip portion 106 in its then-current configuration and/or position and additionally prevent movement and/or articulation of the distal tip portion 106.

The other graphs described above may also be correlated to the configuration of FIG. 12. For example, in some embodiments, when the touch sensor 190 detects the physician's hand and/or the physician's thumb in contact with the handle 102, the actuator 116, and/or the non-motorized and non-ratcheting mechanism, the electrical signal may be interrupted to therefore release the clutch mechanism 150 and/or permit movement and/or articulation of the distal tip portion 106. The graphs shown in FIGS. 8A and 8B may apply in a similar manner to the configuration of FIG. 12, wherein the left side of the graph on FIG. 8A would correspond to the touch sensor 190 detecting the physician's hand and/or the physician's thumb in contact with the handle 102, the actuator 116, and/or the non-motorized and non-ratcheting mechanism. As such, the graphs shown in FIGS. 8A and 8B correspond to the touch sensor 190 detecting the physician's hand and/or the physician's thumb in contact with the handle 102, the actuator 116, and/or the non-motorized and non-ratcheting mechanism, wherein the electrical signal (e.g., voltage) to the clutch mechanism 150 is then changed, such as interrupted and/or no electrical signal (e.g., voltage) is being received by the clutch mechanism 150. As such, the correlation between the touch sensor 190 and the electrical signal may be easily visualized.

Additionally, in some embodiments, the graphs shown in FIGS. 9A and 9B may also apply in a similar manner to the configuration of FIG. 12, the electrical signal (e.g., voltage) sent to and/or received by the clutch mechanism 150 may be gradually changed, such as gradually reduced from the predetermined value V toward and/or to zero in response to a predetermined configuration related to the touch sensor 190. A gradual change (e.g., decrease or increase) in the electrical signal (e.g., voltage) sent to and/or received by the clutch mechanism 150 may produce, cause, and/or correlate to a gradual release by the clutch mechanism 150 such that resistance to movement and/or articulation of the distal tip portion 106 is also gradually reduced and/or released. In this alternate relationship, the clutch mechanism 150 may act as a braking mechanism similar to the configuration(s) described above.

Figure 13:
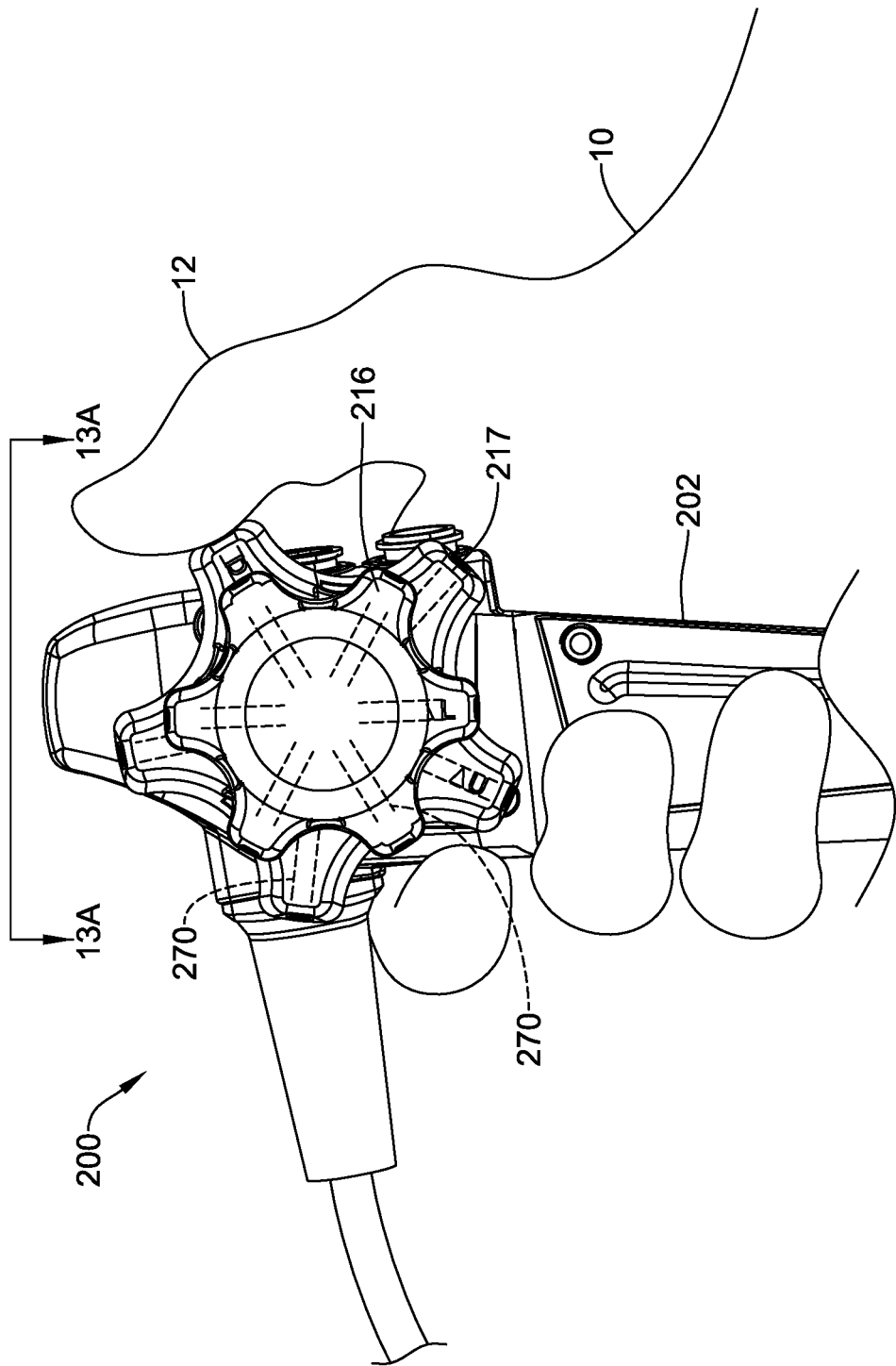
FIG. 13 illustrates selected aspects of a clutch mechanism in the endoscopic system of FIG. 2.

FIG. 13 illustrates an example configuration of the endoscope 200. In some embodiments, a manually applied force may be applied to the first actuator 216 by the physician's hand 10 and/or the physician's thumb 12 (e.g., the manually applied force is being exerted upon the handle 202 and/or the first actuator 216). In some embodiments, the manually applied force may be applied to the second actuator 217 (e.g., the manually applied force is being exerted upon the handle 202 and/or the second actuator 217). In some embodiments, the non-motorized and non-ratcheting mechanism of the endoscope 200 may include a strain gauge 270 configured to detect the manually applied force. In some embodiments, the strain gauge 270 may include one or more strain gauges, at least one strain gauge, and/or a plurality of strain gauges—for example, a first strain gauge disposed on the first actuator 216 and a second strain gauge disposed on the second actuator 217. In some embodiments, the first actuator 216 and/or the second actuator 217 may include the strain gauge 270.

In some embodiments, the first non-motorized and non-ratcheting mechanism may include a first clutch mechanism 250 (e.g., FIG. 13A) actuatable in response to a first electrical signal. The first clutch mechanism 250 may be configured to prevent movement and/or articulation of the distal tip portion 206 in the first plane when the first electrical signal is received by the first clutch mechanism 250, as described herein. In some embodiments, the second non-motorized and non-ratcheting mechanism may include a second clutch mechanism 260 (e.g., FIG. 13A) actuatable in response to a second electrical signal. The second clutch mechanism 260 may be configured to prevent movement and/or articulation of the distal tip portion 206 in the second plane when the second electrical signal is received by the second clutch mechanism 260, as described herein. In some embodiments, the absence of the manually applied force may generate and/or send the first electrical signal to the first clutch mechanism 250 and/or the second electrical signal to the second clutch mechanism 260 to therefore lock the distal tip portion 206 in its then-current configuration and/or position and additionally prevent articulation of the distal tip portion 206.

Figure 13A:
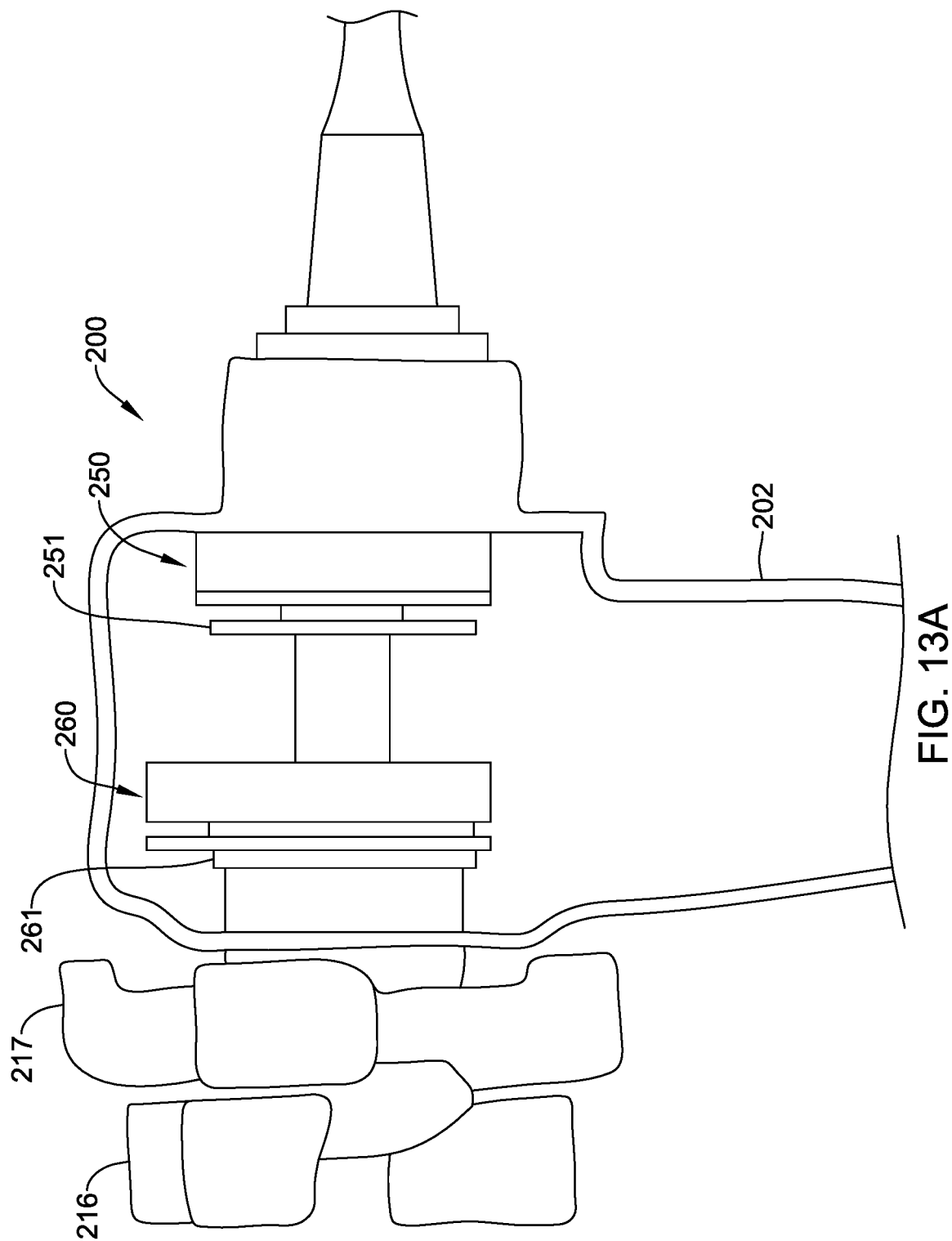
FIG. 13A is a partial cutaway end view of the endoscopic system of FIG. 13.

FIG. 13A is a partial cutaway end view of FIG. 13 illustrating an example configuration of selected internal components of the endoscope 200, the first clutch mechanism 250, and the second clutch mechanism 260. In at least some embodiments, the first clutch mechanism 250 and/or the second clutch mechanism 260 may be constructed in a manner similar to the clutch mechanism 150 described herein, and selected details thereof are not repeated in the interest of brevity.

In some embodiments, when the manually applied force is not being applied to the handle 202 and/or the first actuator 216, the first electrical signal is sent to and/or received by the first clutch mechanism 250, thereby engaging and/or activating the first clutch mechanism 250, as shown in FIG. 13A, to prevent rotation and/or movement of the first pulley 251 relative to the handle 202 and thereby further prevent movement and/or articulation of the distal tip portion 206 in the first plane. Similarly, when the manually applied force is not being applied to the handle 202 and/or the second actuator 217, the second electrical signal is sent to and/or received by the second clutch mechanism 260, thereby engaging and/or activating the second clutch mechanism 260, to prevent rotation and/or movement of the second pulley 261 relative to the handle 202 and thereby further prevent movement and/or articulation of the distal tip portion 206 in the second plane. As shown, and solely for the purpose of illustration, the second clutch mechanism 260 in FIG. 13A is disengaged and/or deactivated, such that rotation and/or movement of the second pulley 261 relative to the handle 202 is permitted and movement and/or articulation of the distal tip portion 206 in the second plane is permitted.

In some embodiments, when the strain gauge 270 fails to detect the manually applied force exerted upon the handle 202, the first actuator 216, and/or the second actuator 217, the logic controller (e.g., a circuit board, for example) may understand this to represent an intent of the physician to lock the distal tip portion 206 in its then-current configuration and/or position, and/or an intent to prevent further movement and/or articulation of the distal tip portion 206. It will be understood that the configuration shown in FIG. 13A is merely representative, and selected components may be re-arranged as needed to accommodate packaging and/or space requirements. For example, in FIG. 13A, the first clutch mechanism 250 and the second clutch mechanism 260 are shown disposed within the handle 202. However, in at least some embodiments, one or both of the first clutch mechanism 250 and the second clutch mechanism 260 may be disposed outside of the handle 202. For example, in some embodiments, the first clutch mechanism 250 and/or the second clutch mechanism 260 may be coupled to and/or engaged with the first actuator 216 and/or the second actuator 217, respectively outside of the handle 202.

Figure 13B:
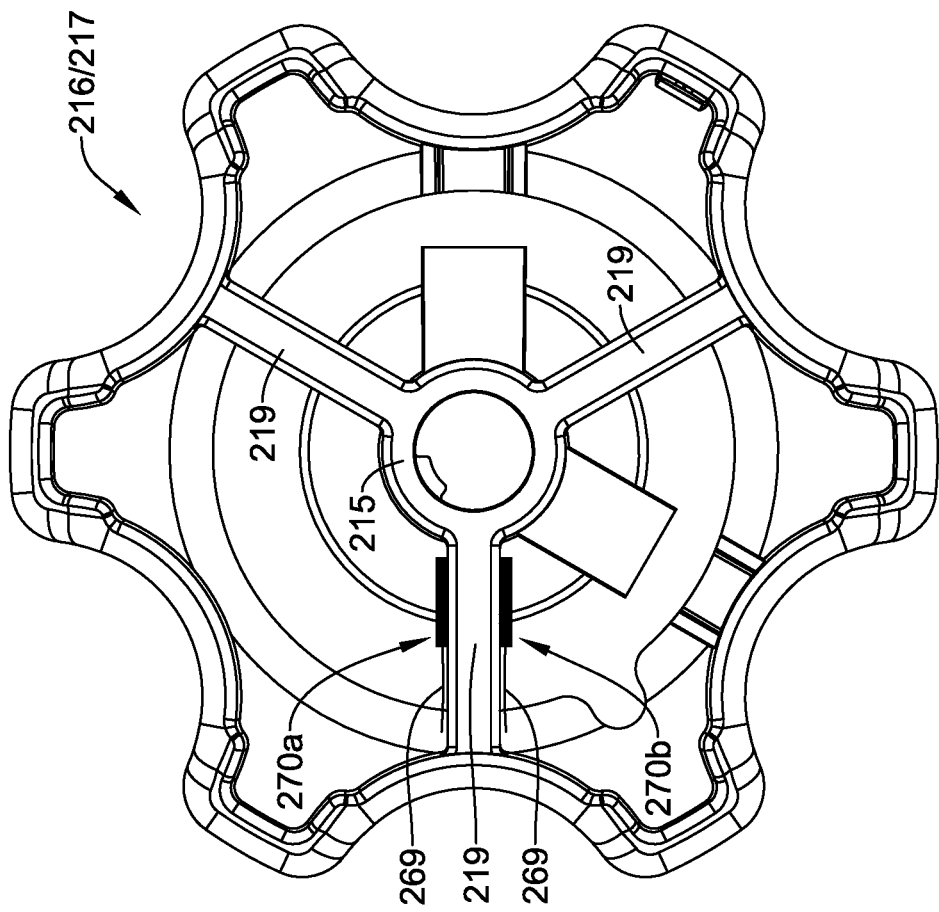
FIG. 13B illustrates selected aspects of the first actuator and/or the second actuator of FIG. 13.

FIG. 13B details selected aspects of an example configuration for the first actuator 216 and/or the second actuator 217. FIG. 13B is shown looking outward from the handle 202 toward a back side or an inside of the first actuator 216 and/or the second actuator 217. As shown in FIG. 13, in some embodiments, the non-motorized and non-ratcheting mechanism of the endoscope 200 may include a strain gauge 270 configured to detect the manually applied force. In some embodiments, the strain gauge 270 may include one or more strain gauges, at least one strain gauge, and/or a plurality of strain gauges—for example, a first strain gauge disposed on the first actuator 216 and a second strain gauge disposed on the second actuator 217. In another example, the first actuator 216 may include a first plurality of strain gauges and/or the second actuator 217 may include a second plurality of strain gauges. In some embodiments, the first actuator 216 and/or the second actuator 217 may include the strain gauge 270.

As shown in FIG. 13B, the first actuator 216 and/or the second actuator 217 may include a plurality of spokes 219 extending radially outward from a central hub 215 to an outer portion of the first actuator 216 and/or the second actuator 217. The plurality of spokes 219 may be and/or may be formed as a plurality of strain concentrating elements. The plurality of strain concentrating elements may be narrowed sections of material that the manually applied force (which the user applies to the outer portion of the first actuator 216 and/or the second actuator 217) must travel through to actuate and/or drive the pulley(s) disposed within the handle 202. A cross-section of the plurality of spokes 219 and/or the plurality of strain concentrating elements may be tuned such that a rotational torque applied to the outer portion of the first actuator 216 and/or the second actuator 217 creates relatively equal bending moments in each of the plurality of spokes 219 and/or the plurality of strain concentrating elements. The strain gauge(s) 270 may be disposed on and/or along the plurality of spokes 219 and/or the plurality of strain concentrating elements near the central hub 215, where the greatest amount of strain occurs. As may be seen in FIG. 13B, in at least some embodiments, a first strain gauge 270a may be disposed on a first side of the plurality of spokes 219 and a second strain gauge 270b may be disposed on a second side of the plurality of spokes 219 opposite the first side. While not all configurations are shown, the first strain gauge 270a and the second strain gauge 270b may be disposed on only one of the plurality of spokes 219, on two or more of the plurality of spokes 219, or on each and every one of the plurality of spokes 219. In some embodiments, the first strain gauge 270a and the second strain gauge 270b may function as a matched pair. When the manually applied force is exerted upon the first actuator 216 and/or the second actuator 217, the strain may be in compression on the first side of the plurality of spokes 219 and the strain may be in tension on the second side of the plurality of spokes 219, or vice versa. Each of the strain gauge(s) 270 (e.g., the first strain gauge 270a, the second strain gauge 270b, etc. may include a signal wire 269 configured to electronically connect the strain gauge(s) 270 with the logic controller to transmit a signal representative of the manually applied force and/or strain on and/or within the plurality of spokes 219 to the logic controller.

FIGS. 14A-14B and 15A-15B are graphs illustrating a relationship between a detected strain and the electrical signal being sent to the first clutch mechanism 250 and/or the second clutch mechanism 260 in the configuration shown in FIG. 13. As may be seen in the graphs, as no strain is detected over time, the electrical signal (e.g., voltage) sent to and/or received by the first clutch mechanism 250 and/or the second clutch mechanism 260 remains generally constant at a predetermined value V. As in the above examples, a predetermined range, band, and/or deviation for registering strain on the strain gauge 270 may be within plus or minus 5.0%, 3.0%, 2.5%, 2.0%, 1.0%, 0.5%, etc. of a desired or expected value. Within the predetermined range, band, and/or deviation, the logic controller may register no change in strain. In the illustrated examples, the dashed line corresponds to the strain gauge 270 (e.g., the first strain gauge) associated with the first clutch mechanism 250 and/or the first actuator 216, and the solid line corresponds to the strain gauge 270 (e.g., the second strain gauge) associated with the second clutch mechanism 260 and/or the second actuator 217. As such, the correlation between the lack of strain detected using the strain gauge(s) 270 and the electrical signal may be easily visualized.

In one example, FIGS. 14A and 14B show that as strain is detected on and/or within the first actuator 216 (e.g., the first knob was rotated) above a threshold amount, the first electrical signal is interrupted and/or the first electrical signal changes, such as from the predetermined value V toward and/or to zero. In other instances, the first electrical signal may increase or decrease from its value when the strain is below the threshold amount. Since the second actuator 217 has had no strain applied to it (e.g., the second knob was not rotated), the second electrical signal remains unchanged (e.g., uninterrupted) and is received by the second clutch mechanism 260 at the predetermined value V. As such, the first clutch mechanism 250 is released to permit movement and/or articulation of the distal tip portion 206 in the first plane while the second clutch mechanism 260 remains engaged to prevent movement and/or articulation of the distal tip portion 206 in the second plane.

Figure 15A:
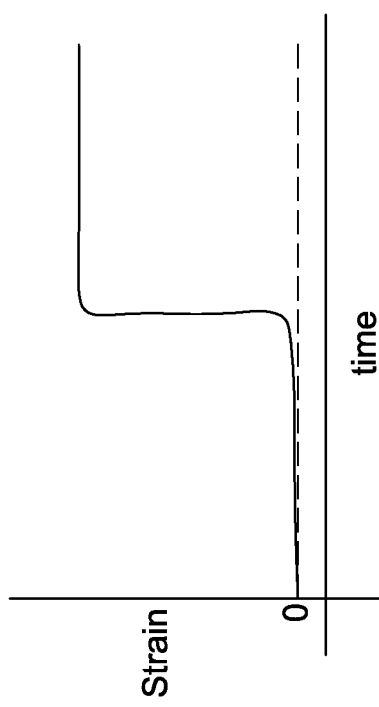
FIGS. 15A-15B are graphs illustrating interactions between different characteristics of the clutch mechanism of FIGS. 13-13A.
Figure 15B:
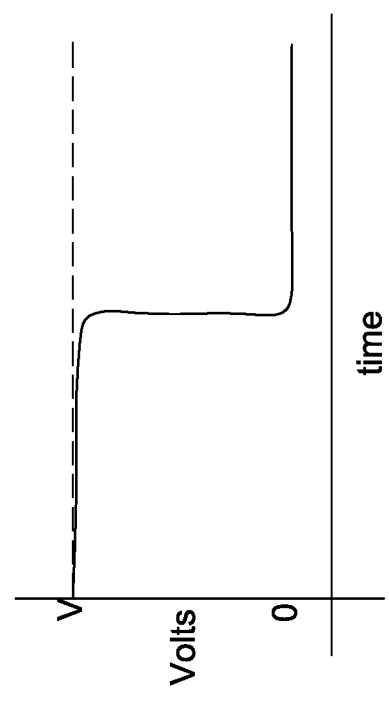

In another example, FIGS. 15A and 15B show that as strain is detected on and/or within the second actuator 217 (e.g., the second knob was rotated) above a threshold amount, the second electrical signal is interrupted and/or the second electrical signal changes, such as from the predetermined value V toward and/or to zero. In other instances, the second electrical signal may increase or decrease from its value when the strain is below the threshold amount. Since the first actuator 216 has had no strain applied to it (e.g., the first knob was not rotated), the first electrical signal remains uninterrupted and is received by the first clutch mechanism 250 at the predetermined value V. As such, the second clutch mechanism 260 is released to permit movement and/or articulation of the distal tip portion 206 in the second plane while the first clutch mechanism 250 remains engaged to prevent movement and/or articulation of the distal tip portion 206 in the first plane.

FIGS. 16A-16B and 17A-17B are graphs illustrating a relationship between the detected strain and the electrical signal being sent to the first clutch mechanism 250 and/or the second clutch mechanism 260 in the configuration shown in FIG. 13. As in the above examples, a predetermined range, band, and/or deviation for registering strain on the strain gauge 270 may be within plus or minus 5.0%, 3.0%, 2.5%, 2.0%, 1.0%, 0.5%, etc. of a desired or expected value. Within the predetermined range, band, and/or deviation, the logic controller may register no change in strain. In the illustrated examples, the dashed line corresponds to the strain gauge 270 (e.g., the first strain gauge) associated with the first clutch mechanism 250 and/or the first actuator 216, and the solid line corresponds to the strain gauge 270 (e.g., the second strain gauge) associated with the second clutch mechanism 260 and/or the second actuator 217. As such, the correlation between the lack of strain detected using the strain gauge(s) 270 and the electrical signal may be easily visualized.

As may be seen in the graphs, as strain is gradually increased and/or detected over time, the electrical signal (e.g., voltage) sent to and/or received by the first clutch mechanism 250 and/or the second clutch mechanism 260 may be gradually changed, such as gradually reduced from the predetermined value V toward and/or to zero. A gradual increase in strain and/or a gradual change, (e.g., decrease or increase) in the electrical signal (e.g., voltage) sent to and/or received by the first clutch mechanism 250 and/or the second clutch mechanism 260 may produce, cause, and/or correlate to a gradual release by the first clutch mechanism 250 and/or the second clutch mechanism 260 such that resistance to movement and/or articulation of the distal tip portion 206 in the first plane and/or the second plane, respectively, is also gradually reduced and/or released. In this alternate relationship, the first clutch mechanism 250 and/or the second clutch mechanism 260 may each act as a braking mechanism for its respective pulley 251/261, wherein a higher strain detected and/or more manually applied force F indicates an intent to move and/or articulate the distal tip portion 206 further and/or faster than a lower strain detected and/or less manually applied force F. However, as above, when the manually applied force F is released and/or removed, the first clutch mechanism 250 and/or the second clutch mechanism 260 may immediately lock the distal tip portion 206 in its then-current configuration and/or position and thereby prevent further movement and/or articulation of the distal tip portion 206 in the first plane and/or the second plane, respectively.

Figure 16A:
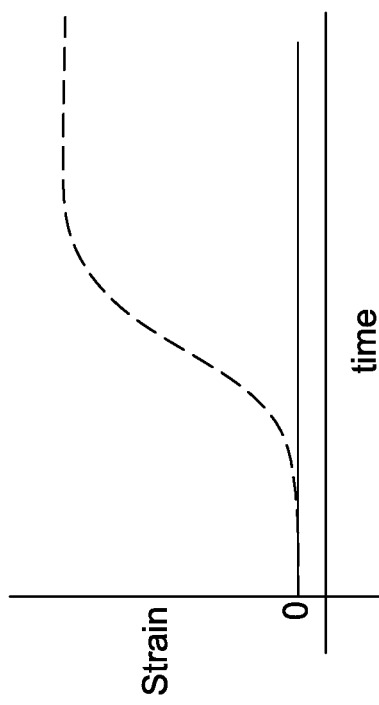
FIGS. 16A-16B are graphs illustrating interactions between different characteristics of the clutch mechanism of FIGS. 13-13A.
Figure 16B:
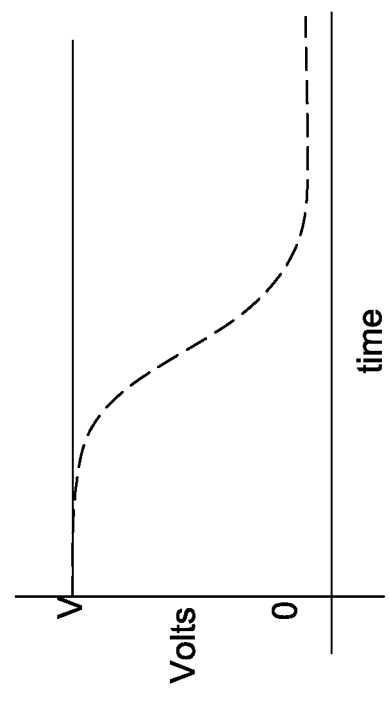

In one example, FIGS. 16A and 16B show that as strain is detected on and/or within the first actuator 216 (e.g., the first knob was rotated) above a threshold amount, the first electrical signal gradually changes, such as from the predetermined value V toward and/or to zero. Since the second actuator 217 has had no strain applied to it (e.g., the second knob was not rotated), the second electrical signal remains unchanged (e.g., uninterrupted) and is received by the second clutch mechanism 260 at the predetermined value V. As such, the first clutch mechanism 250 is gradually released to permit movement and/or articulation of the distal tip portion 206 in the first plane while the second clutch mechanism 260 remains engaged to prevent movement and/or articulation of the distal tip portion 206 in the second plane.

Figure 17A:
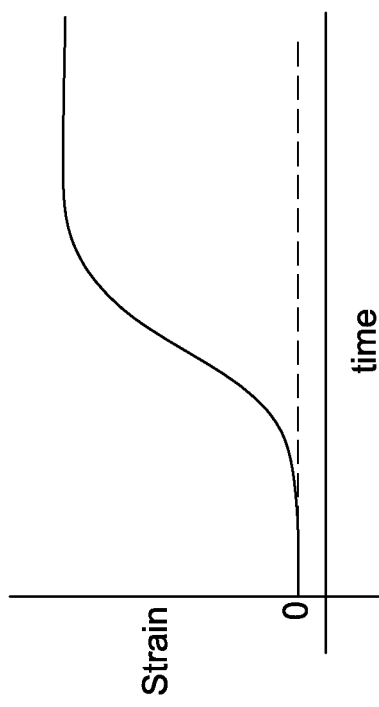
FIGS. 17A-17B are graphs illustrating interactions between different characteristics of the clutch mechanism of FIGS. 13-13A.
Figure 17B:
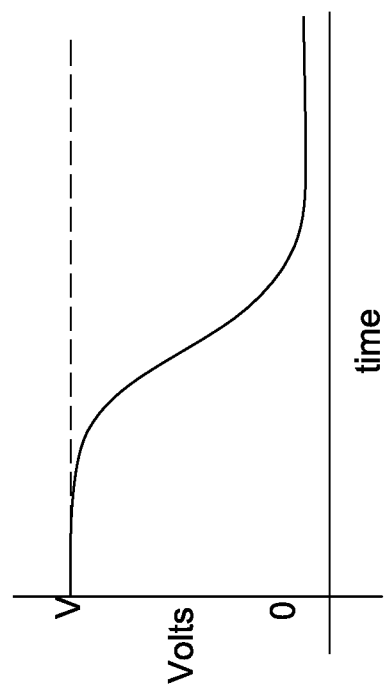

In another example, FIGS. 17A and 17B show that as strain is detected on and/or within the second actuator 217 (e.g., the second knob was rotated) about a threshold amount, the second electrical signal gradually changes, such as gradually changes from the predetermined value V toward and/or to zero. Since the first actuator 216 has had no strain applied to it (e.g., the first knob was not rotated), the first electrical signal remains unchanged (e.g., uninterrupted) and is received by the first clutch mechanism 250 at the predetermined value V. As such, the second clutch mechanism 260 is gradually released to permit movement and/or articulation of the distal tip portion 206 in the second plane while the first clutch mechanism 250 remains engaged to prevent movement and/or articulation of the distal tip portion 206 in the first plane.

Figure 18:
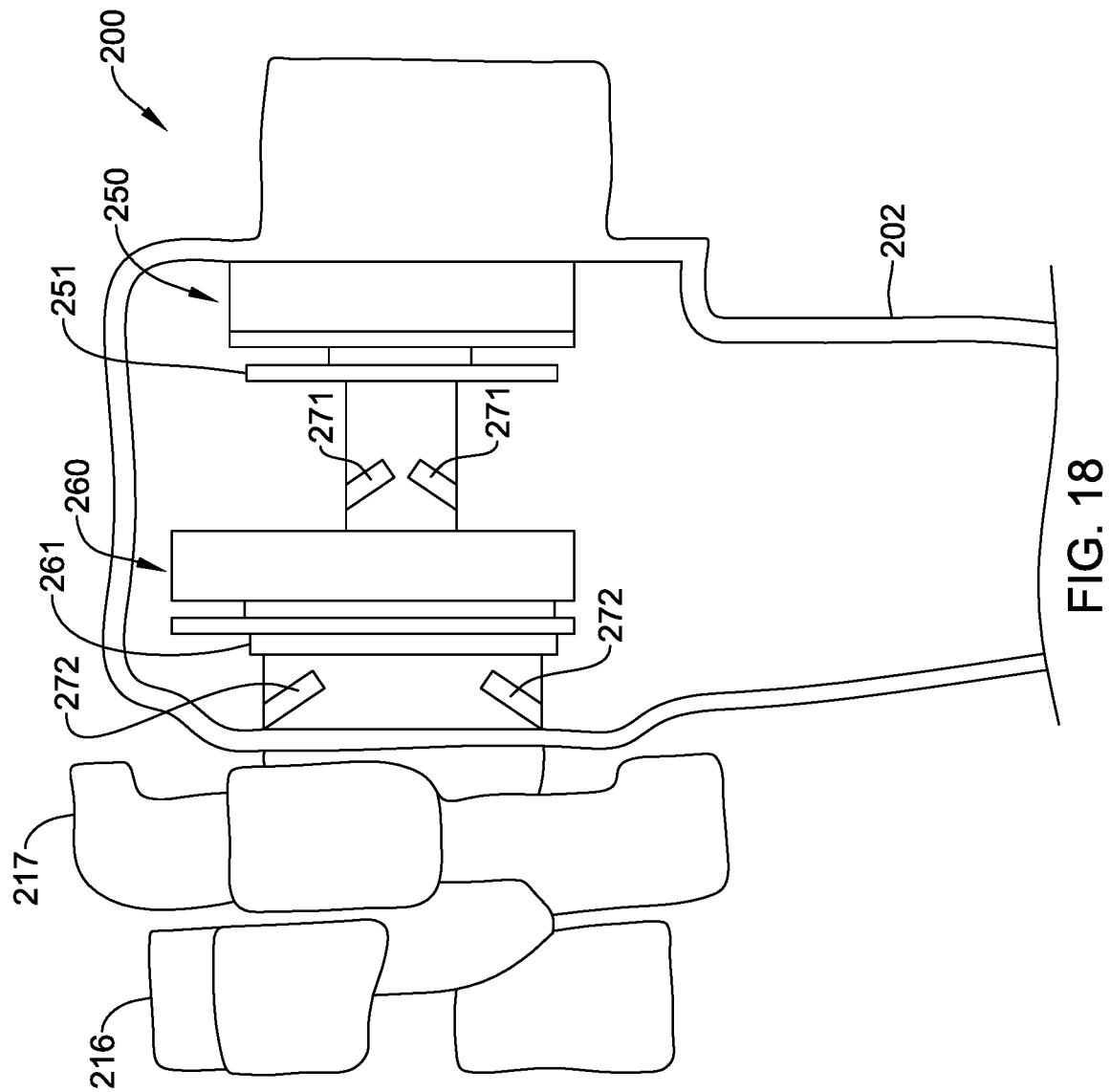
FIG. 18 is a partial cutaway end view showing an alternative configuration of a clutch mechanism of the endoscopic system of FIG. 13.

FIG. 18 is a partial cutaway end view of FIG. 13 illustrating another example configuration of selected internal components of the endoscope 200, the first clutch mechanism 250, and the second clutch mechanism 260. In at least some embodiments, the first clutch mechanism 250 and/or the second clutch mechanism 260 may be constructed in a manner similar to the clutch mechanism 150 described herein, and selected details thereof are not repeated in the interest of brevity. In the configuration of FIG. 18, a first strain gauge 271 may be disposed on and/or may be a part of a first shaft coupling the first actuator 216 to the first pulley 251, and/or a second strain gauge 272 may be disposed on and/or may be a part of a second shaft coupling the second actuator 217 to the second pulley 261. In some embodiments, the endoscope 200 may include only the first strain gauge 271, or the endoscope 200 may include only the second strain gauge 272, or the endoscope 200 may include both the first strain gauge 271 and the second strain gauge 272. Other aspects of the example of FIG. 18 may be similar to and/or the same as that of FIG. 13 and/or FIG. 13A. In some embodiments, combinations of the strain gauge 270, the first strain gauge 271, the strain gauge 272, and/or other configurations of the strain gauge(s) disclosed herein are also contemplated.

Figure 19:
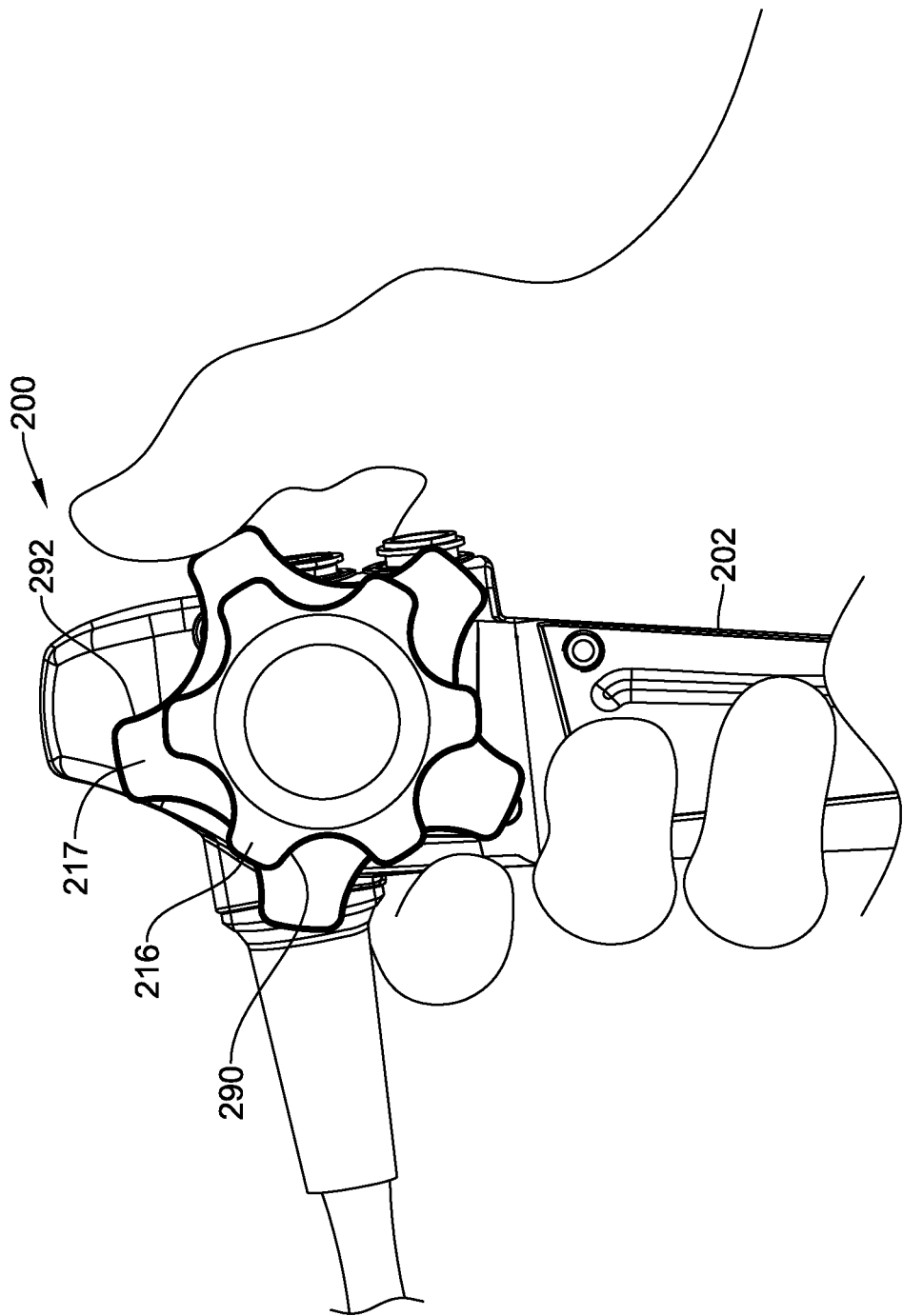
FIG. 19 illustrates selected aspects of an alternative configuration of a clutch mechanism in the endoscopic system of FIG. 2.

FIG. 19 illustrates another example configuration of the endoscope 200. In FIG. 19, the endoscope 200 may include a first touch sensor 290 associated with and/or disposed on the first actuator 216, and a second touch sensor 292 associated with and/or disposed on the second actuator 217.

In some embodiments, the first non-motorized and non-ratcheting mechanism of the endoscope 200 may include the first touch sensor 290 configured to detect a user or a physician's hand in contact with the first non-motorized and non-ratcheting mechanism. In some embodiments, the first touch sensor 290 may be configured to detect the physician's thumb in contact with the first actuator 216. In some embodiments, the first touch sensor 290 may include a touch-sensitive resistive strip disposed on an outer surface of the first actuator 216. In some embodiments, the first touch sensor 290 may include one or more touch sensors, at least one touch sensor, and/or a plurality of touch sensors. In some embodiments, the first actuator 216 may include the first touch sensor 290 disposed thereon, as shown in FIG. 19 for example. In some embodiments, the first touch sensor 290 may be disposed on a radially outward surface, an outwardly facing surface, and/or a circumferential surface of the first actuator 216. Other configurations are also contemplated.

In some embodiments, the second non-motorized and non-ratcheting mechanism of the endoscope 200 may include the second touch sensor 292 configured to detect a user or a physician's hand in contact with the second non-motorized and non-ratcheting mechanism. In some embodiments, the second touch sensor 292 may be configured to detect the physician's thumb in contact with the second actuator 217. In some embodiments, the second touch sensor 292 may include a touch-sensitive resistive strip disposed on an outer surface of the second actuator 217. In some embodiments, the second touch sensor 292 may include one or more touch sensors, at least one touch sensor, and/or a plurality of touch sensors. In some embodiments, the second actuator 217 may include the second touch sensor 292 disposed thereon, as shown in FIG. 19 for example. In some embodiments, the second touch sensor 292 may be disposed on a radially outward surface, an outwardly facing surface, and/or a circumferential surface of the second actuator 217. Other configurations are also contemplated.

In some embodiments, the first touch sensor 290 may be configured to change (e.g., interrupt) the first electrical signal (e.g., voltage) being sent to the first clutch mechanism 250 when the first touch sensor 290 detects the physician's hand and/or the physician's thumb in contact with the handle 202, the first actuator 216, and/or the first non-motorized and non-ratcheting mechanism, and the first electrical signal (e.g., voltage) may be sent to and/or received by the first clutch mechanism 250 when the first touch sensor 290 fails to detect the physician's hand and/or the physician's thumb in contact with the handle 202, the first actuator 216, and/or the first non-motorized and non-ratcheting mechanism. In some embodiments, the second touch sensor 292 may be configured to change (e.g., interrupt) the second electrical signal (e.g., voltage) being sent to and/or received by the second clutch mechanism 260 when the second touch sensor 292 detects the physician's hand and/or the physician's thumb in contact with the handle 202, the second actuator 217, and/or the second non-motorized and non-ratcheting mechanism, and the second electrical signal (e.g., voltage) may be sent to and/or received by the second clutch mechanism 260 when the second touch sensor 290 fails to detect the physician's hand and/or the physician's thumb in contact with the handle 202, the second actuator 217, and/or the second non-motorized and non-ratcheting mechanism.

In some embodiments, when the first touch sensor 290 fails to detect the physician's hand and/or the physician's thumb in contact with the handle 202, the first actuator 216, and/or the first non-motorized and non-ratcheting mechanism, the first electrical signal may be sent to and/or received by the first clutch mechanism 250 to therefore lock the distal tip portion 206 in its then-current configuration and/or position within the first plane and additionally prevent movement and/or articulation of the distal tip portion 206 within the first plane. In some embodiments, when the second touch sensor 292 fails to detect the physician's hand 10 and/or the physician's thumb 12 in contact with the handle 202, the second actuator 217, and/or the second non-motorized and non-ratcheting mechanism, the second electrical signal may be sent to and/or received by the second clutch mechanism 260 to therefore lock the distal tip portion 206 in its then-current configuration and/or position within the second plane and additionally prevent movement and/or articulation of the distal tip portion 206 within the second plane.

The graphs shown in FIGS. 14A-14B and FIGS. 15A-15B may apply in a similar manner to the configuration of FIG. 19, wherein detection of the physician's hand and/or the physician's thumb in contact with the first touch sensor 290 corresponds to a strain applied to the first actuator 216 and detection of the physician's hand and/or the physician's thumb in contact with the second touch sensor 292 corresponds to a strain applied to the second actuator 217. In the context of FIG. 19, the dashed line would correspond to the first touch sensor 290 associated with the first clutch mechanism 250 and/or the first actuator 216, and the solid line would correspond to the second touch sensor 292 associated with the second clutch mechanism 260 and/or the second actuator 217.

For example, in the context of FIG. 19, the graph on FIG. 14A would correspond to the second touch sensor 292 failing to detect the physician's hand and/or the physician's thumb in contact with the handle 102, the second actuator 217, and/or the second non-motorized and non-ratcheting mechanism. The graphs shown in FIGS. 14A and 14B correspond to the physician's hand and/or the physician's thumb not being in contact with the second touch sensor 292, wherein the second electrical signal (e.g., voltage) is being sent to the second clutch mechanism 260 at the predetermined value V to engage the second clutch mechanism 260 and/or to lock the distal tip portion 206 in its then-current configuration and/or position within the second plane and additionally prevent movement and/or articulation of the distal tip portion 206 within the second plane. Additionally, the graph on FIG. 14A would correspond to the first touch sensor 290 detecting the physician's hand and/or the physician's thumb in contact with the handle 102, the first actuator 216, and/or the first non-motorized and non-ratcheting mechanism, wherein the first electrical signal (e.g., voltage) may be changed (e.g., interrupted) to therefore release the first clutch mechanism 250 and/or permit movement and/or articulation of the distal tip portion 206 within the first plane.

In the context of FIG. 19, the left side of the graph on FIG. 15A would correspond to the first touch sensor 290 failing to detect the physician's hand and/or the physician's thumb in contact with the handle 102, the first actuator 216, and/or the first non-motorized and non-ratcheting mechanism. The graphs shown in FIGS. 15A and 15B correspond to the physician's hand and/or the physician's thumb not being in contact with the first touch sensor 290, wherein the first electrical signal (e.g., voltage) is being sent to the first clutch mechanism 250 at the predetermined value V to engage the first clutch mechanism 250 and/or to lock the distal tip portion 206 in its then-current configuration and/or position within the first plane and additionally prevent movement and/or articulation of the distal tip portion 206 within the first plane. Additionally, the graph on FIG. 15A would correspond to the second touch sensor 292 detecting the physician's hand and/or the physician's thumb in contact with the handle 102, the second actuator 217, and/or the second non-motorized and non-ratcheting mechanism, wherein the second electrical signal may be changed (e.g., interrupted) to therefore release the second clutch mechanism 260 and/or permit movement and/or articulation of the distal tip portion 206 within the second plane.

Additionally, in some embodiments, the graphs shown in FIGS. 16A-16B and 17A-17B may also apply in a similar manner to the configuration and context of FIG. 19. In some embodiments, the first electrical signal (e.g., voltage) sent to and/or received by the first clutch mechanism 250 may be gradually changed, such as reduced from the predetermined value V toward and/or to zero, in response to a predetermined configuration related to the first touch sensor 290. A gradual change, such as a gradual reduction in the first electrical signal (e.g., voltage) sent to and/or received by the first clutch mechanism 250 may produce, cause, and/or correlate to a gradual release by the first clutch mechanism 250 such that resistance to movement and/or articulation of the distal tip portion 206 in the first plane is also gradually reduced and/or released. In this alternate relationship, the first clutch mechanism 250 may act as a braking mechanism similar to the configuration(s) described above. Similarly, in some embodiments, the second electrical signal (e.g., voltage) sent to and/or received by the second clutch mechanism 260 may be gradually changed, such as gradually reduced from the predetermined value V toward and/or to zero, in response to a predetermined configuration related to the second touch sensor 292. A gradual change (e.g., increase or decrease) in the second electrical signal (e.g., voltage) sent to and/or received by the second clutch mechanism 260 may produce, cause, and/or correlate to a gradual release by the second clutch mechanism 260 such that resistance to movement and/or articulation of the distal tip portion 206 in the second plane is also gradually reduced and/or released. In this alternate relationship, the second clutch mechanism 260 may act as a braking mechanism similar to the configuration(s) described above.

Figure 20:
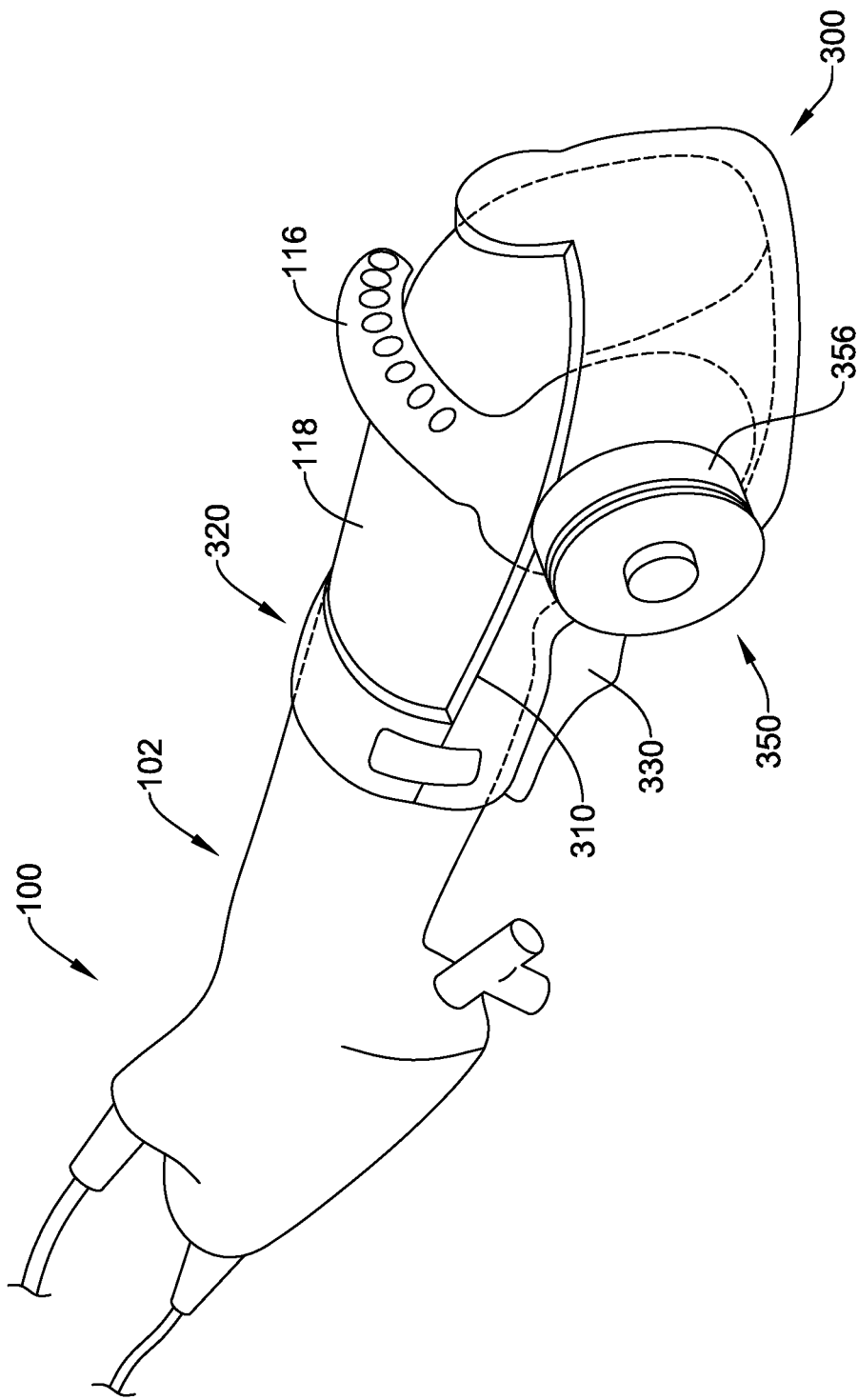
FIG. 20 illustrates selected aspects of an accessory clutch system with the endoscopic system of FIGS. 1A-1B.

In some embodiments, the disclosure relates to an accessory clutch system 300 for use with articulating endoscopes (e.g., the endoscope 100, etc.). One example of the accessory clutch system 300 may be seen in FIG. 20. In some embodiments, the accessory clutch system 300 may include a housing 310 configured to matingly attach to the handle 102 of the endoscope 100, wherein the handle 102 includes a non-motorized and non-ratcheting mechanism configured to articulate the distal tip portion 106 (not shown in FIG. 20). It will be appreciated that the illustrated embodiment is merely exemplary and the accessory clutch system 300 may be designed for use with other articulating endoscopes and/or handles thereof. In some embodiments, the non-motorized and non-ratcheting mechanism may include the actuator 116. In some embodiments, the actuator 116 may be movably coupled to the handle 102. In some embodiments, the actuator 116 may be configured to engage with and/or actuate the non-motorized and non-ratcheting mechanism. The distal tip portion 106 may be articulatable in response to a manually applied force exerted upon the handle 102 and/or the actuator 116. The accessory clutch system 300 may be configured such that removal of the manually applied force locks the distal tip portion 106 in its then-current configuration and/or position.

In some embodiments, the accessory clutch system 300 may include a clutch mechanism 350 secured to the housing 310, wherein the clutch mechanism 350 may be configured to releasably engage the actuator 116 of the endoscope 100, wherein the actuator 116 is disposed on an exterior of the handle 102 of the endoscope 100. For example, an exterior surface of the clutch mechanism 350 may releasably and/or matingly engage with an outer surface and/or an outer contour of the actuator 116.

In at least some embodiments, the housing 310 may include a retaining structure 320 configured to encircle at least a portion of the handle 102 of the endoscope 100. In some embodiments, the retaining structure 320 may include a strap. In some embodiments, the retaining structure 320 may include a latch. In some embodiments, the retaining structure 320 may include a removable element configured to be releasably engaged to the housing 102. In some embodiments, the removable element may include a hook and loop closure (e.g., Velcro®, etc.), an elastic member having a hook on one or both ends and a corresponding aperture or apertures in the housing 310, or other suitable structures. In some embodiments, the retaining structure 320 may be disposed adjacent a distal end of the housing 310 and may be configured to encircle at least a portion of the grip area 118 of the handle 102. Other configurations are also contemplated.

In some embodiments, the clutch mechanism 350 may be actuatable in response to an electrical signal, wherein the clutch mechanism 350 is configured to prevent movement and/or articulation of the distal tip portion 106 of the endoscope 100 when the electrical signal is set to and/or received by the clutch mechanism 350, thereby effectively locking the distal tip portion 106 in its then-current configuration and/or position. In some embodiments, the clutch mechanism 350 may be configured to release when the electrical signal is changed, such as interrupted and/or when the electrical signal is not received by the clutch mechanism 350, thereby permitting movement and/or articulation of the distal tip portion 106 of the endoscope 100 in the absence of the electrical signal.

In some embodiments, the clutch mechanism 350 may include a clutch housing 356 configured to non-rotatably couple the clutch mechanism 350 to the housing 310. The clutch mechanism 350 may be constructed in a manner and/or using components similar to and/or the same as the clutch mechanism 150 discussed herein. An armature and a rotor may be disposed within the clutch housing 356. The armature may be non-rotatably engaged with the clutch housing 356. The rotor may be configured to rotate freely with respect to the armature and/or the clutch housing 356 when the electrical signal is at a first level, or in the absence of the electrical signal and/or when the clutch mechanism 350 fails to receive the electrical signal. Conversely, the rotor may be configured to lock to and/or relative to the armature when the electrical signal changes from the first level to a second level different from the first level, such as when an electrical signal greater than zero is received by the clutch mechanism 350. In at least some embodiments, when the electrical signal is received by the clutch mechanism 350, the rotor becomes energized and develops a magnetic attraction to the armature. When the rotor engages the armature, the rotor shaft 354 is prevented from rotating, which in turn prevents rotation of the actuator 116. As such, the clutch mechanism 350 is configured to prevent articulation of the distal tip portion 106 when the electrical signal is received by the clutch mechanism 350, thereby effectively locking the distal tip portion 106 in its then-current configuration and/or position.

In at least some embodiments, the accessory clutch system 300 and/or the clutch mechanism 350 may include and/or may be connectable to a power source. In some embodiments, the power source may be a battery or other self-contained power source disposed within the clutch housing 356. In some embodiments, the power source may be a battery or other self-contained power source disposed within a cover disposed over the clutch mechanism 350 and/or the clutch housing 356. In some embodiments, the accessory clutch system 300 and/or the clutch mechanism 350 may be electrically connectable to the handle 102 of the endoscope 100 to receive electrical power therefrom.

In some embodiments, a strain gauge may be configured to detect the manually applied force. In some embodiments, the strain gauge may include one or more strain gauges, at least one strain gauge, and/or a plurality of strain gauges. In some embodiments, the strain gauge may be incorporated into the clutch mechanism 350 and is configured to detect the manually applied force being transmitted by the actuator 116. In some embodiments, the strain gauge may be a secondary feature that is added to the handle 102 and/or the actuator 116 when the housing 310 is secured to and/or engaged with the handle 102. In some embodiments, the electrical signal may change (e.g., be interrupted) in response to a strain detected using the strain gauge. As such, the clutch mechanism 350 may be released when the strain gauge detects the manually applied force above a threshold amount, thereby permitting articulation of the distal tip portion 106.

In some embodiments, when the strain gauge detects the manually applied force exerted upon the handle 102 and/or the actuator 116 about a threshold amount, the logic controller (e.g., a circuit board, for example) may understand this to represent an intent of the physician to move and/or articulate the distal tip portion 106 from its then-current configuration and/or position, and/or an intent further move and/or articulate the distal tip portion 106. In some embodiments, as strain is detected over time, the electrical signal (e.g., voltage) sent to and/or received by the clutch mechanism 350 may change, for example, be interrupted and drop from the predetermined value toward and/or to zero.

In some embodiments, as strain is gradually increased and/or detected over time, the electrical signal (e.g., voltage) sent to and/or received by the clutch mechanism 350 may gradually change, such as be gradually reduced from the predetermined value toward and/or to zero. A gradual increase in strain and/or a gradual change (e.g., increase or decrease) in the electrical signal (e.g., voltage) sent to and/or received by the clutch mechanism 350 may produce, cause, and/or correlate to a gradual release by the clutch mechanism 350 such that resistance to movement and/or articulation of the distal tip portion 106 is also gradually reduced and/or released. In such a relationship, the clutch mechanism 350 may act as a braking mechanism, wherein a higher strain detected and/or more manually applied force indicates an intent to move and/or articulate the distal tip portion 106 further and/or faster than a lower strain detected and/or less manually applied force. However, as above, when the manually applied force is released and/or removed, the clutch mechanism 350 may immediately lock the distal tip portion 106 in its then-current configuration and/or position and thereby prevent further movement and/or articulation of the distal tip portion 106.

In some embodiments, the housing 310 includes an actuatable button 330 disposed thereon. In some embodiments, the actuatable button 330 may include one or more actuatable buttons, at least one actuatable button, and/or a plurality of actuatable buttons. In some embodiments, the actuatable button 330 may be configured to change (e.g., interrupt) the electrical signal (e.g., voltage) being sent to and/or received by the clutch mechanism 350 when the actuatable button 330 is in a depressed position relative to the electrical signal (e.g., voltage) that may be sent to the clutch mechanism 350 when the actuatable button 330 is in a released position.

In some embodiments, the actuatable button 330 may be configured as a trigger to be actuated by a physician's finger while the actuator 116 is configured to be actuated and/or moved by the physician's thumb. Other configurations are also contemplated. A position of the actuatable button 330 may function similar to and/or in the same manner as the strain gauge described above. Alternatively, a strain gauge may be included on the actuatable button 330 in a manner similar to the strain gauge described above.

In some embodiments, when the actuatable button 330 is in the released position (e.g., zero strain on the actuatable button 330), the electrical signal (e.g., voltage) may be sent to and/or received by the clutch mechanism 350 at the predetermined value to engage the clutch mechanism 350 and/or to lock the distal tip portion 106 in its then-current configuration and/or position and additionally prevent movement and/or articulation of the distal tip portion 106. In some embodiments, when the actuatable button 330 is in the depressed position (e.g., strain on the actuatable button 330), the electrical signal may change (e.g., may be interrupted) to therefore release and/or disengage the clutch mechanism 350 and/or permit movement and/or articulation of the distal tip portion 106. For example, when the actuatable button 330 is in the depressed position (e.g., strain on the actuatable button 330), the electrical signal (e.g., voltage) to the clutch mechanism 350 may be interrupted and/or no electrical signal (e.g., voltage) may be received by the clutch mechanism 350.

Additionally, in some embodiments, when the actuatable button 330 is gradually moved toward and/or to depressed position (e.g., strain on the actuatable button 330), the electrical signal (e.g., voltage) to the clutch mechanism 350 may be gradually changed (e.g., interrupted). As the position of the actuatable button 330 moves toward the depressed position (e.g., strain is gradually increased and/or detected over time), the electrical signal (e.g., voltage) sent to and/or received by the clutch mechanism 350 may be gradually changed, such as gradually reduced from the predetermined value toward and/or to zero. A gradual change in position of the actuatable button 330 (e.g., a gradual increase in strain) and/or a gradual change (e.g., increase or decrease) in the electrical signal (e.g., voltage) sent to and/or received by the clutch mechanism 350 may produce, cause, and/or correlate to a gradual release by the clutch mechanism 350 such that resistance to movement and/or articulation of the distal tip portion 106 is also gradually reduced and/or released. In this alternate relationship, the clutch mechanism 350 may act as a braking mechanism similar to the configuration(s) described above.

Figure 21:
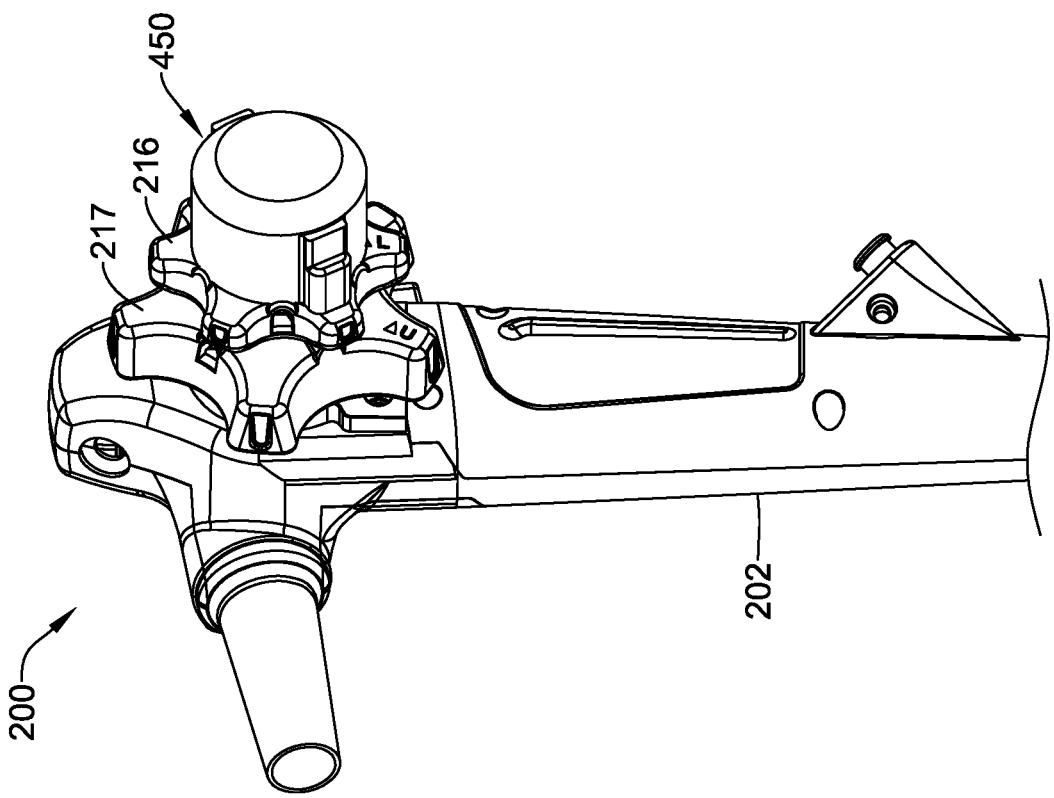
FIGS. 21-22 illustrate selected aspects of an alternative configuration of a clutch mechanism that may be associated with the endoscopic systems of FIGS. 2, 13, and/or 19.
Figure 22:
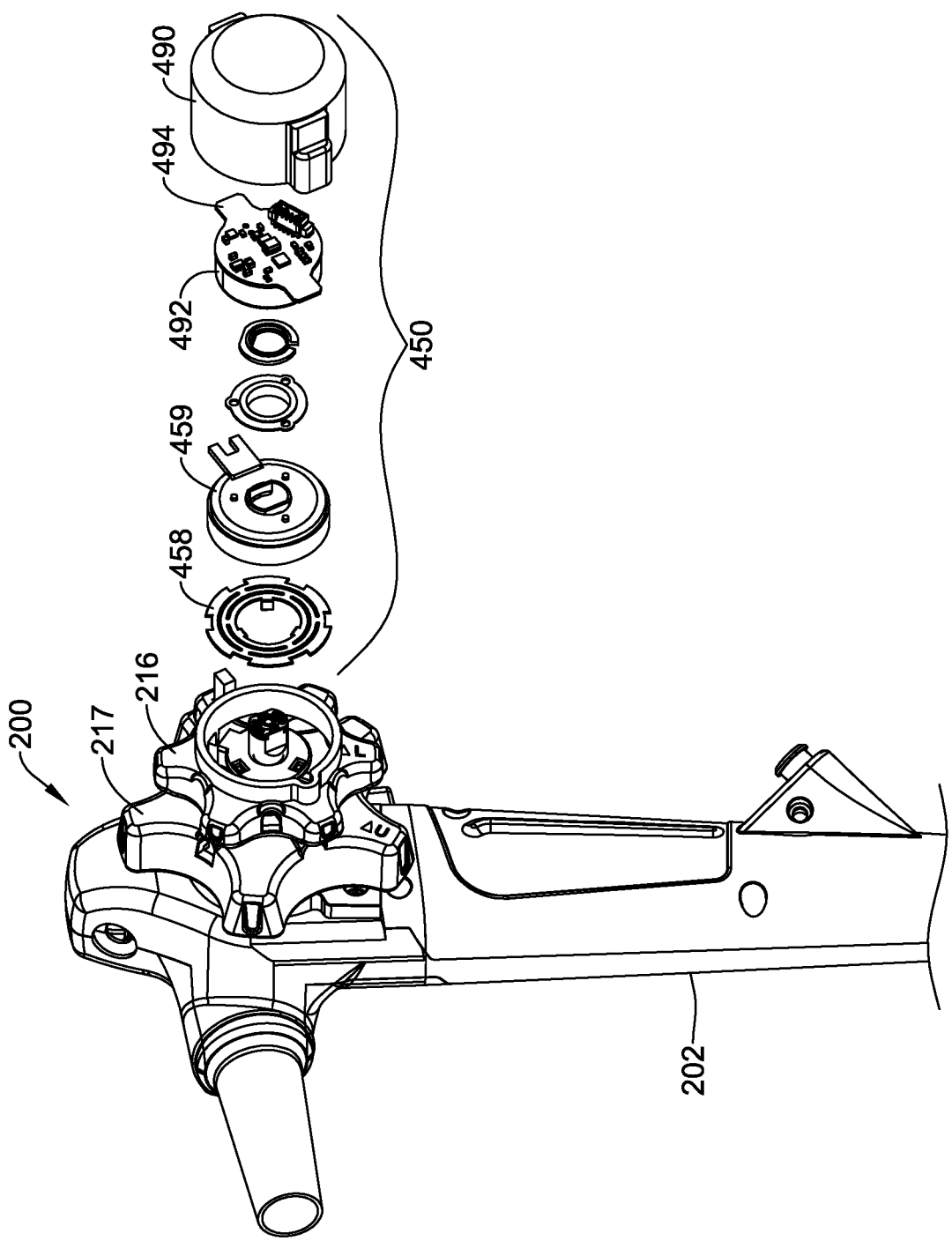

FIGS. 21-22 illustrate an alternative configuration of an endoscopic system including the endoscope 200, as described herein, wherein the non-motorized and non-ratcheting mechanism includes a clutch mechanism 450 actuatable in response to an electrical signal. The clutch mechanism 450 may be configured to prevent articulation of the distal tip portion 206 of the endoscope 200 in the first plane when the electrical signal is sent to and/or received by the clutch mechanism 450.

In the configuration of FIGS. 21-22, the first actuator 216 may include the clutch mechanism 450 mounted thereon and/or coupled thereto. In the configuration of FIGS. 21-22, the clutch mechanism 450 may be disposed outside of the housing 202 of the endoscope 200. For example, the clutch mechanism 450 may be coupled to the first actuator 216 outside of the housing 202.

In some embodiments, the clutch mechanism 450 may include an armature 458 (e.g., a clutch disk) non-rotatably engaged with the first actuator 216. The armature 458 may be formed from a metallic material and/or a magnetically responsive material. In some embodiments, the armature 458 may include a plurality of protrusions configured to engage and/or be received by a corresponding plurality of receptacles formed in the first actuator 216. In at least some embodiments, the armature 458 may be fixedly attached to the first actuator 216. In some embodiments, the clutch mechanism 450 may include a rotor 459, wherein the rotor 459 is configured to rotate freely with respect to the armature 458 at a first electrical signal level, or in the absence of the electrical signal and/or when the clutch mechanism 450 fails to receive the electrical signal, and a coil (not shown) disposed within the rotor 459, wherein the coil is non-rotatably coupled to the first actuator 216. As such, the rotor 459 may be configured to rotate relative to the coil and/or the first actuator 216 at the first electrical signal level, or in the absence of the electrical signal and/or when the clutch mechanism 450 fails to receive the electrical signal.

Conversely, the rotor 459 may be configured to lock to and/or relative to the armature 458 when the electrical signal changes from the first electrical signal level to a second electrical signal level different from the first electrical signal level, or when an electrical signal is received by the clutch mechanism 450. In at least some embodiments, when the electrical signal changes or is received by the clutch mechanism 450, the coil and/or the rotor 459 becomes energized and develops a magnetic attraction to the armature 458. When the rotor 459 engages the armature 458, the rotor shaft is prevented from rotating, which in turn prevents rotation of the first actuator 216. As such, the clutch mechanism 450 is configured to prevent articulation of the distal tip portion 206 in the first plane when the second electrical signal level is received by the clutch mechanism 450 or when the electrical signal is received by the clutch mechanism 450, thereby effectively locking the distal tip portion 206 in its then-current configuration and/or position within the first plane.

In some embodiments, the clutch mechanism 450 may be configured to operate and/or function in an inverse manner to that described above. For example, in some embodiments, the rotor 459 may be configured to lock to and/or relative to the armature 458 in the absence of the electrical signal and/or when the clutch mechanism 450 fails to receive the electrical signal. As such, the clutch mechanism 450 may be configured to prevent articulation of the distal tip portion 206 when no electrical signal is received by the clutch mechanism 450, thereby locking the distal tip portion 206 in its then-current configuration and/or position. In some embodiments, when the electrical signal is received by the clutch mechanism 450, the rotor 459 becomes de-energized (and/or a magnetic polarity of the rotor 459 is reversed) and magnetic attraction to the armature 458 is terminated to release the clutch mechanism 450 and allow articulation of the distal tip portion 206. Accordingly, the rotor 459 may be configured to rotate freely with respect to the armature 158 when the electrical signal is received by the clutch mechanism 450, thereby permitting and/or enabling movement of the distal tip portion 206.

In some embodiments, the clutch mechanism 450 may include a battery 492 and/or a control board 494 such that the clutch mechanism 450 may be substantially self-contained within a cover 490 coupled to the first actuator 216. In at least some embodiments, the cover 490 may be removably coupled to the first actuator 216 to permit access to one or more components of the clutch mechanism 450 for service and/or replacement of the one or more components. In some embodiments, the cover 490 may be fixedly attached to the first actuator 216. In some embodiments, the clutch mechanism 450 may be electrically coupled to a power source external to the clutch mechanism 450 (e.g., the endoscope 200, an external battery, etc.).

In some embodiments, the endoscope 200 having the clutch mechanism 450 may include a second non-motorized and non-ratcheting mechanism including a second clutch mechanism actuatable in response to an electrical signal, as described herein. The second clutch mechanism may be configured to prevent articulation of the distal tip portion 206 of the endoscope 200 in the second plane when the electrical signal is sent to and/or received by the second clutch mechanism 450. In some embodiments, the second non-motorized and non-ratcheting mechanism may include the second actuator 217, and the second clutch mechanism may be configured to selectively engage the second actuator 217 as described herein. In some embodiments, the second clutch mechanism may be disposed within the housing 202 of the endoscope 200. Other configurations are also contemplated.

In some embodiments, the clutch mechanism(s) and/or endoscope(s) described herein may include one or more safety mechanisms configured to prevent tissue damage and/or damage to the endoscope itself. For example, the endoscope(s) may include one or more features intended to prevent the endoscope from damaging tissue if it is "locked" in a curved or deflected configuration and the user attempted to pull the endoscope out of the patient's anatomy. In some embodiments, the endoscope(s) may include on/off indicators (e.g., lights, LEDs, etc.) showing the user whether or not the clutch mechanism is engaged and/or locked, and/or whether or not the feature is enabled or disabled. In some embodiments, the endoscope(s) may include a pressure sensor or other feedback device on the distal tip portion. In one example, the pressure sensor or other feedback device may cause the clutch mechanism to disengage and/or release to allow movement of the distal tip portion if the pressure on the distal tip portion exceeds a predetermined threshold. Alternatively, a strain gauge on the cable, wire, or filament engaged with the pulley, or optical strain gauge fibers, may be used to infer pressure exerted by the endoscope on adjacent tissue. In any case, a safety threshold for pressure or strain may be an adjustable input variable that the user is able to choose and/or adjust before and/or during the procedure. When the pressure or strain exceeds the safety threshold, the clutch mechanism may completely disengage and/or release, or it may dynamically partially disengage to maintain the pressure or strain at or just below the safety threshold. In some embodiments, the user may choose between these options as another user input factor. In some embodiments, there may be more than one pressure or strain safety threshold. For example, there may be a first safety threshold to ensure pressure or strain does not exceed a threshold when the user is not engaging and/or actuating the actuator (e.g., when advancing or retracting the endoscope). In some embodiments, there may be a second safety threshold that produces an audible and/or a visible alarm warning the user of potential harm when they are activating the actuator(s). In some embodiments, the maximum allowable pressure or strain (e.g., the safety threshold) may be a function of the shape of the endoscope body and/or the distal tip portion, and/or a function of the position of the endoscope within the patient's anatomy. For example, real-time shape sensing of the endoscope may be enabled using a Fiber Bragg grating optical fiber or other optical fibers. In some embodiments, the safety threshold(s) may be activated and/or deactivated by users via voice commands, buttons on the endoscope, touchscreen controls, or other methods. In some embodiments, the clutch mechanism(s) may be activated and/or deactivated, locked and/or released, etc. to using voice or other controls at any time by the user.

In some embodiments, the clutch mechanism(s) and/or endoscope(s) described herein may be used in conjunction and/or cooperation with a robotically actuated surgical system. For example, the clutch mechanism(s) and/or endoscope(s) described herein may be useful for holding the distal tip portion in position during a tool change. Other configurations and/or uses associated with robotics are also contemplated.

In some embodiments, the clutch mechanism(s) and/or the endoscope(s) described herein may include a configuration where a proportional and/or a variable level of control over the distal tip portion may be applied and/or used. In some embodiments, the clutch mechanism(s) and/or a brake may be quickly flipped on and off. In some embodiments, the clutch mechanism(s) and/or the brake may receive and/or be subjected to a proportional electrical signal that directly affects the loading on the clutch mechanism(s) and/or the brake. For example, the endoscopic system may be configured to place the endoscope in a training configuration where it may be more difficult to move the control knob(s) when the user is not following an optimal motion. In another example, the endoscopic system may be configured in a way that makes it more difficult to position and/or place the endoscope(s) and/or the distal tip portion in a configuration that would damage tissue and/or the endoscope itself. Other configurations are also contemplated.

In some embodiments, the clutch mechanism(s) and/or the endoscope(s) described herein may include a position sensor (e.g., a potentiometer, an encoder, a hall effect sensor, etc.) which may be incorporated into the control of the electrical signal. The position sensor may be configured to change a threshold at which the electrical signal causes the clutch mechanism(s) to lock and/or release. In some instances, at full articulation of the distal tip portion, the actuator(s) could be permitted to rotate in a backwards direction (thus permitting the distal tip portion to move back toward a neutral configuration) before the clutch mechanism(s) re-engages if the logic controller waits until the manually applied force and/or the strain detected on the actuator(s) returns to zero. A slight or minor modification of the point at which the electrical signal is sent to the clutch mechanism(s), or is interrupted (depending on the embodiment/configuration), may engage the clutch mechanism(s) before all of the manually applied force is removed so that the actuator(s) is not permitted to move and/or actuate the distal tip portion. That is, the position sensor may be used to modify the electrical signal such that the distal tip portion may be locked in its position and/or configuration before the manually applied force is fully and/or completely removed.

In some embodiments, the use of the clutch mechanism(s) may also refer to the use of a brake or other means of impeding motion or applied force. A clutch may be considered a mechanical device that engages or disengages transmission of torque or force, often through applied contact pressure. In some embodiments, a dedicated brake may be used in place of or in addition to the clutch mechanism(s).

Those skilled in the art will recognize that embodiments of the present disclosure may be manifested in a variety of forms other than the specific embodiments described and contemplated herein. Accordingly, departure in form and detail may be made without departing from the scope and spirit of the present disclosure as described in the appended claims.

The materials that can be used for the various components of the system(s) and the various elements thereof disclosed herein may include those commonly associated with medical devices. For simplicity purposes, the following discussion refers to the system. However, this is not intended to limit the devices and methods described herein, as the discussion may be applied to other elements, members, components, or devices disclosed herein, such as, but not limited to, the handle(s), the elongate shaft(s), the actuator(s), the clutch mechanism(s), the pulley(s), the rotatable knob(s), the lever(s), the actuatable button(s), the distal tip portion(s), the housing, etc., and/or elements or components thereof.

In some embodiments, the system, and/or components thereof, may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

In at least some embodiments, portions or all of the system, and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the system in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system to achieve the same result.

In some embodiments, a degree of Magnetic Resonance Imaging (MRI) compatibility is imparted into the system and/or other elements disclosed herein. For example, the system, and/or components or portions thereof, may be made of a material that does not substantially distort the image and create substantial artifacts (i.e., gaps in the image). Certain ferromagnetic materials, for example, may not be suitable because they may create artifacts in an MRI image. The system, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the present disclosure. This may include, to the extent that it is appropriate, the use of any of the features of one example embodiment being used in other embodiments. The scope of the present disclosure is, of course, defined in the language in which the appended claims are expressed.

What is claimed is:
1. An endoscopic system, comprising:
an endo scope including a handle and an elongate shaft extending distally therefrom;
wherein the handle includes a non-motorized and non-ratcheting mechanism configured to articulate a distal tip portion of the elongate shaft;
wherein the non-motorized and non-ratcheting mechanism includes an actuator disposed on an exterior of the handle;
wherein the distal tip portion is articulatable in response to a manually applied force exerted upon the actuator;
wherein removal of the manually applied force locks the distal tip portion in its then-current configuration regardless of a then-current position of the actuator;
wherein the non-motorized and non-ratcheting mechanism includes a clutch mechanism actuatable in response to an electrical signal, the clutch mechanism being configured to prevent articulation of the distal tip portion when the electrical signal is changed.

2. The endoscopic system of claim 1, wherein the actuator includes a rotatable knob configured to articulate the distal tip portion.

3. The endoscopic system of claim 1, wherein the actuator includes a lever configured to articulate the distal tip portion.

4. The endoscopic system of claim 1, wherein the non-motorized and non-ratcheting mechanism includes a strain gauge configured to detect the manually applied force exerted upon the actuator.

5. The endoscopic system of claim 4, wherein the electrical signal is changed in response to a strain detected using the strain gauge.

6. The endoscopic system of claim 5, wherein the clutch mechanism is released when the manually applied force is detected using the strain gauge.

7. The endoscopic system of claim 1, wherein the non-motorized and non-ratcheting mechanism includes a touch sensor configured to detect a user's hand in contact with the actuator.

8. The endoscopic system of claim 1, wherein the endo scope includes an actuatable button disposed on the handle, the actuatable button being configured to change the electrical signal to the clutch mechanism when the actuatable button is depressed.

9. The endoscopic system of claim 8, wherein the electrical signal is sent to the clutch mechanism when the actuatable button is released.

10. An endoscopic system, comprising:
an endo scope including a handle and an elongate shaft extending distally therefrom;
wherein the handle includes:
a first non-motorized and non-ratcheting mechanism configured to articulate a distal tip portion of the elongate shaft in a first plane, the first non-motorized and non-ratcheting mechanism includes an actuator configured to be manipulated by a user and a first clutch mechanism actuatable in response to a first electrical signal;
wherein the distal tip portion is articulatable in response to a manually applied force exerted upon the actuator;
wherein removal of the manually applied force alters the first electrical signal received by the first clutch mechanism to thereby lock the distal tip portion in its then-current configuration and prevent articulation of the distal tip portion in the first plane.

11. The endoscopic system of claim 10, wherein the handle further comprises a second non-motorized and non-ratcheting mechanism configured to articulate the distal tip of the elongate shaft in a second plane different from the first plane.

12. The endoscopic system of claim 10, wherein the second non-motorized and non-ratcheting mechanism includes a second clutch mechanism actuatable in response to a second electrical signal, the second clutch mechanism being configured to prevent articulation of the distal tip portion in the second plane when the second electrical signal is received.

13. An accessory clutch system for use with articulating endoscopes, comprising:
a housing configured to matingly attach to an exterior of a handle of an endoscope, wherein the handle includes a non-motorized and non-ratcheting mechanism configured to articulate a distal tip portion; and
a clutch mechanism secured to the housing;
wherein the clutch mechanism is configured to releasably engage an actuator of the endoscope;
wherein the actuator is disposed on the exterior of the handle;
wherein the housing includes a retaining structure configured to engage at least a portion of the exterior of the handle;
wherein the distal tip portion is articulatable in response to a manually applied force exerted upon the handle;
wherein removal of the manually applied force locks the distal tip portion in its then-current configuration;
wherein the clutch mechanism is actuatable in response to an electrical signal, the clutch mechanism being configured to prevent articulation of the distal tip portion when the electrical signal is at a first signal level; and
wherein a strain gauge is configured to detect the manually applied force.

14. The accessory clutch system of claim 13, wherein the electrical signal is changed from the first signal level to a second signal level in response to a strain detected using the strain gauge.

15. The accessory clutch system of claim 13, wherein the housing includes an actuatable button disposed thereon, the actuatable button being configured to change the electrical signal to the clutch mechanism from the first signal level to a second signal level when the actuatable button is depressed.

16. The accessory clutch system of claim 15, wherein the first signal level is sent to the clutch mechanism when the actuatable button is released.

* * * * *